(12) United States Patent
Cheng

(10) Patent No.: US 10,995,067 B2
(45) Date of Patent: May 4, 2021

(54) TREATMENT OF FABRY DISEASE

(71) Applicant: Academia Sinica, Taipei (TW)

(72) Inventor: Wei-Chieh Cheng, Taipei (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 16/313,057

(22) PCT Filed: Jun. 14, 2017

(86) PCT No.: PCT/US2017/037381
§ 371 (c)(1),
(2) Date: Dec. 24, 2018

(87) PCT Pub. No.: WO2017/222881
PCT Pub. Date: Dec. 28, 2017

(65) Prior Publication Data
US 2019/0225579 A1  Jul. 25, 2019

Related U.S. Application Data

(60) Provisional application No. 62/354,139, filed on Jun. 24, 2016.

(51) Int. Cl.
| | | |
|---|---|---|
| *A61K 31/7028* | (2006.01) | |
| *C07D 207/02* | (2006.01) | |
| *C07D 207/12* | (2006.01) | |
| *A61K 31/40* | (2006.01) | |
| *A61K 45/06* | (2006.01) | |
| *A61P 3/00* | (2006.01) | |
| *A61K 38/47* | (2006.01) | |

(52) U.S. Cl.
CPC ............ *C07D 207/02* (2013.01); *A61K 31/40* (2013.01); *A61K 31/7028* (2013.01); *A61K 38/47* (2013.01); *A61K 45/06* (2013.01); *A61P 3/00* (2018.01); *C07D 207/12* (2013.01); *C12Y 302/01022* (2013.01)

(58) Field of Classification Search
CPC .................................................. A61K 31/7028
See application file for complete search history.

(56) References Cited

U.S. PATENT DOCUMENTS

2011/0237538 A1* 9/2011 De Moor ............... A61K 31/40
514/53

OTHER PUBLICATIONS

PubChem CID 12103488, National Center for Biotechnology Information. PubChem Database. CID=12103488, https://pubchem.ncbi.nlm.nih.gov/compound/12103488 (accessed on Nov. 5, 2019)), create date Feb. 7, 2007. (Year: 2007).*
Shabbeer et al., Molecular Genetics and Metabolism, 76, 2002, pp. 23-30. (Year: 2002).*
CHEMBL3350086, National Center for Biotechnology Information. PubChem Database. CID=12103488, https://pubchem.ncbi.nlm.nih.gov/ compound/12103488 (accessed on Jul. 20, 2020), create date Feb. 7, 2007.
Cheng et al., "From Natural Product-Inspired Pyrrolidine Scaffolds to the Development of New Human Golgi a-Mannosidase II Inhibitors", 2013, Chemistry, 8: 2600-2604.
Florence et al, "Syntheses and Glycosidase Inhibitory Activities of 2-(Aminomethyl)-5-(hydroxymethyl)pyrrolidine-3,4-diol Derivatives", 2004; Helvetica Chimica Acta, 87: 800-810.
Cheng et al, "Rapid preparation of (3R,4S,5R) polyhydroxylated pyrrolidine-based libraries to discover a pharmacological chaperone for treatment of Fabry disease", 2016 European Journal of Medicinal Chemistry, 126: 1-6.

* cited by examiner

*Primary Examiner* — Laura L Stockton

(57) ABSTRACT

Disclosed herein are novel uses of a polyhydroxylated pyrrolidine for the manufacture of a medicament for treating Fabry disease (FD). Accordingly, the present disclosure provides a method of treating a subject having or suspected of having FD. The method includes the step of, administering to the subject a therapeutically effective amount of a compound of formula (I), a salt, an ester or a solvate thereof, wherein: $R_1$ is H, or $C_{1-3}$ amine optionally substituted with —$COR_2$; $R_2$ is alkyl or alkene optionally substituted with cycloalkyl or phenyl having at least one substituent selected from the group consisting of, halo, alkyl, haloalkyl, and alkoxyl; so as to ameliorate, alleviate mitigate and/or prevent symptoms associated with the FD. According to preferred embodiments of the present disclosure, the compound of formula (I) is a chaperon of a mutated human lysosomal α-galactosidase A (α-Gal A).

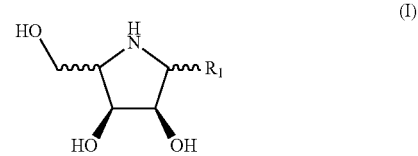

(I)

11 Claims, 6 Drawing Sheets
Specification includes a Sequence Listing.

a)

b)

a)

b)

a)

b)

a)

b)

SEQUENCE LISTING

```
<160> NUMBER OF SEQ ID NOS: 8

<210> SEQ ID NO 1
<211> LENGTH: 31
<212> TYPE: DNA
<213> ORGANISM: Artificial Sequence
<220> FEATURE:
<223> OTHER INFORMATION: forward primer

<400> SEQUENCE: 1
aggtcggatc cgacaatgca gctgaggaac c                            31

<210> SEQ ID NO 2
<211> LENGTH: 39
<212> TYPE: DNA
<213> ORGANISM: Artificial Sequence
<220> FEATURE:
<223> OTHER INFORMATION: reverse primer

<400> SEQUENCE: 2
ggtggaattc ttaaagtaag tcttttaatg acatctgca                    39

<210> SEQ ID NO 3
<211> LENGTH: 38
<212> TYPE: DNA
<213> ORGANISM: Artificial Sequence
<220> FEATURE:
<223> OTHER INFORMATION: N215S-F_primer

<400> SEQUENCE: 3
ggccctttca aaagcccagt tatacagaaa tccgacag                     38

<210> SEQ ID NO 4
<211> LENGTH: 38
<212> TYPE: DNA
<213> ORGANISM: Artificial Sequence
<220> FEATURE:
<223> OTHER INFORMATION: N215S-R_primer
```

```
<400> SEQUENCE: 4
ctgtcggatt tctgtataac tgggcttttg aaagggcc                              38

<210> SEQ ID NO 5
<211> LENGTH: 39
<212> TYPE: DNA
<213> ORGANISM: Artificial Sequence
<220> FEATURE:
<223> OTHER INFORMATION: Q279E-F_primer

<400> SEQUENCE: 5
tttggcctca gctggaatga gcaagtaact cagatggcc                             39

<210> SEQ ID NO 6
<211> LENGTH: 39
<212> TYPE: DNA
<213> ORGANISM: Artificial Sequence
<220> FEATURE:
<223> OTHER INFORMATION: Q279E-R_primer

<400> SEQUENCE: 6
ggccatctga gttacttgct cattccagct gaggccaaa                             39

<210> SEQ ID NO 7
<211> LENGTH: 39
<212> TYPE: DNA
<213> ORGANISM: Artificial Sequence
<220> FEATURE:
<223> OTHER INFORMATION: R301Q-F_primer

<400> SEQUENCE: 7
ttcatgtcta atgacctcca acacatcagc cctcaagcc                             39

<210> SEQ ID NO 8
<211> LENGTH: 39
<212> TYPE: DNA
<213> ORGANISM: Artificial Sequence
<220> FEATURE:
<223> OTHER INFORMATION: R301Q-R_primer

<400> SEQUENCE: 8
ggcttgaggg ctgatgtgtt ggaggtcatt agacatgaa                             39
```

TREATMENT OF FABRY DISEASE

CROSS-REFERENCES TO RELATED APPLICATIONS

This application claims the benefit of U.S. Provisional Application Ser. No. 62/354,139 filed Jun. 24, 2016; the entire content of which is incorporated herein by reference.

BACKGROUND OF THE INVENTION

1. Field of the Invention

The present disclosure in general relates to the field of pharmacological chaperons; more particularly to the derivatives of naturally occurring polyhydroxylated pyrrolidines, and their use in the treatment or prophylaxis of Fabry disease.

2. Description of Related Art

Fabry disease (FD) is an inherited lysosomal metabolic disorder, and more than 300 missense mutations in the GLA gene have been identified. The corresponding mutant proteins are subject to degradation by the process of Endoplasmic reticulum (ER) quality control; thus the activity of lysosomal α-galactosidase A (α-Gal A) is deficient and results in progressive accumulation of neutral glycosphingolipids with terminal α-galactosyl residue, globotriaosylceramide (GL-3) in cells. Patients of FD suffered from symptoms like chronic neuronopathic pain, gastrointestinal disturbances, angiokeratoma, cardiomyopathy, and premature myocardial infarctions. To date, FD is one of the most common lysosomal storage diseases (LSDs) and the incidence of FD was initially estimated to be 1 in 476,000 to 117,000 live births though this prevalence may be underestimated. Surprisingly, recent study showed a high frequency of Taiwanese males with FD in the newborn screening tests was 1 in 1,250.

Enzyme replacement therapy (ERT) with recombinant human α-Gal A (rh-α-Gal A) is now available for the treatment of FD and in most patients, ERT renders clinical improvement or stabilization of diseases. However, ERT is limited by its high cost, inconvenience, and instability of the enzyme protein in blood and lack of the ability to cross the blood-brain barrier (BBB). Moreover, the infused recombinant enzymes tend to be unstable at neutral pH, resulting in a short-circulating half-life of the properly folded active enzyme in vivo. Thus, development of new approaches toward treatment of FD or improve the efficacy of rh-α-Gal A is urgently needed.

An emerging strategy for the treatment of LSDs, which called chemical (or pharmacological) chaperone therapy, has been reported, in which small molecules are used to assist the folding of mutant enzymes to prevent their degradation by quality control in the ER prior to transfer to lysosome. 1-Deoxygalactonojirimycin (DGJ), a six-membered iminosugar with potent inhibitory activity against α-Gal A, has been demonstrated as an effective pharmacological chaperone to restore the mutant α-Gal A in Fabry cells and tissues. Recent announcement of the positive outcome of phase III trial of Migalastat (DGJ) strongly suggests that chemical chaperone may be a better alternative for the treatment of FD. Most reported chemical chaperones for Fabry patients with α-Gal A mutations are DGJ-based derivatives or piperidine-typed iminosugars. In contrast, five-membered iminosugars as chemical chaperons for FD have not been extensively studied. Recent results showed no promising molecules as inhibitors or activators toward α-Gal A via a high throughput screening approach (approximately 230,000 compounds). The scarcity of reported information results in delaying the development of new chemical chaperones for the treatment of FD.

Naturally occurring polyhydroxylated pyrrolidines, e.g., 2,5-dideoxy-2,5-imido-d-mannitol (DMDP) are a class of compounds that exhibit inhibitory activities toward various glycosidases. For example, the key inventor of the present disclosure has found a new DMDP-based chemical chaperone for Gaucher disease that enhances lysosomal α-glucosidase (GCase) activity (Cheng et al., Bioorg. Med. Chem. 2013, 21, 5021). Further, a recent study also reported that three DMDP stereoisomers including 2,5-dideoxy-2,5-imido-d-altritol (DIA), C4-epimer DGDP (DGDP is a 2-epimer of DMDP), and C3-epimer DGDP, exhibit good inhibitory activity against α-Gal (coffee bean) (Ayers et al., J. Org. Chem. 2012, 77, 7777).

In the present disclosure, the inventors further investigated the use of various stereoisomers and derivatives of a naturally occurring polyhydroxylated pyrrolidine (i.e., amino-DMDP or ADMDP) as molecular chaperons for the treatment or prophylaxis of FD.

SUMMARY

The present disclosure is based on unexpected discovery that certain ADMDP and derivatives thereof are potent α-Gal A inhibitors, and may assist the folding of mutant α-Gal A, thus these compounds may serve as molecular chaperons to mutantα-Gal A and therefor are useful for the development of medicaments for the treatment or prophylaxis of FD.

Accordingly, the present disclosure is directed to a method of treating a subject having or suspected of having FD. The method includes the step of, administering to the subject a therapeutically effective amount of a compound of formula (I), a salt, an ester or a solvate thereof,

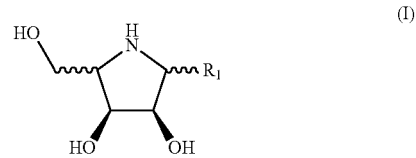

(I)

Wherein:
R₁ is H or $C_{1-3}$ amine optionally substituted with —COR₂; and
R₂ is alkyl or alkene optionally substituted with cycloalkyl or phenyl having at least one substituent selected from the group consisting of, halo, alkyl, haloalkyl, and alkoxyl; so as to ameliorate, alleviate, mitigate and/or prevent symptoms associated with the Fabry disease, so as to ameliorate, alleviate mitigate and/or prevent symptoms associated with the FD.

According to some embodiments of the present disclosure, the compound of formula (I) is capable of suppressing α-GAL A activity.

According to other embodiments of the present disclosure, the compound of formula (I) is chaperon of a human lysosomal α-galactosidase A (α-Gal A) mutant.

According to preferred embodiments of the present disclosure, the human α-Gal A mutant comprises a mutation selected from the group consisting of, R112H, P205T, Q279E, R301Q, R356W, and R363C.

According to preferred embodiments of the present disclosure, the compound of formula (I) is selected from the group consisting of,

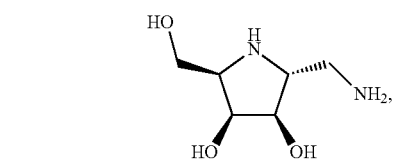
17

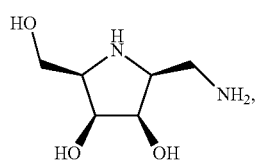
18

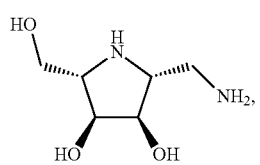
19

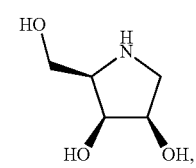
28

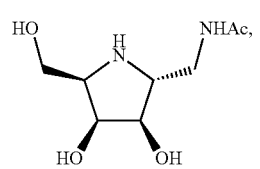
29

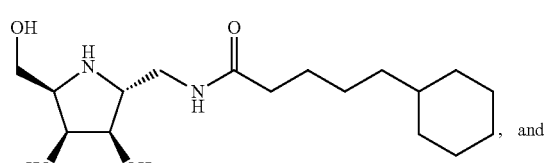
33
, and

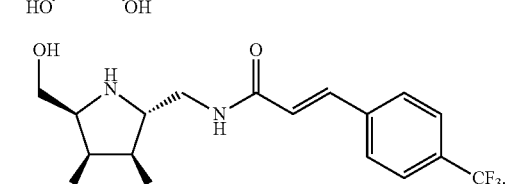
37

According to one preferred embodiment, the compound of formula (I) is

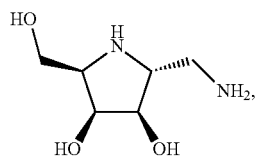
17

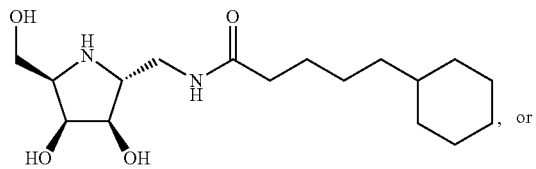
33
, or

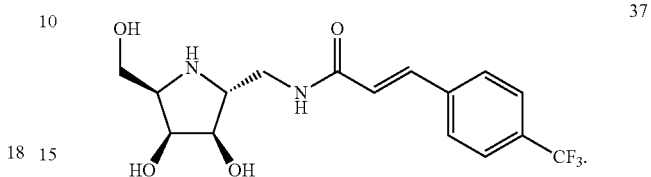
37

According to embodiments of the present disclosure, the compound of formula (I) is administered to the subject in the amount of 0.001-500 g/day, preferably in the amount of about 0.05-450 g/day.

According to some preferred embodiments, the method further includes the step of administering to the subject a therapeutically effective amount of human α-Gal A, prior to, concurrently with, or after the administration of the compound of formula (I).

Another aspect of the present disclosure is directed to novel ADMDP derivatives having the structure of formula (I-1),

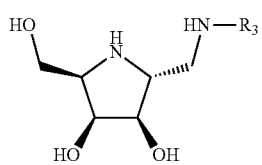
(I-1)

Wherein,

R₃ is H or —COR₂; and

R₂ is alkyl or alkene optionally substituted with cycloalkyl, or phenyl having at least one substituent selected from the group consisting of, halo, alkyl, haloalkyl, and alkoxyl.

According to one preferred embodiment, the compound of formula (I-1) is

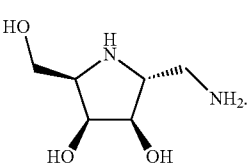
17

According to another preferred embodiment, the compound of formula (I-1) is

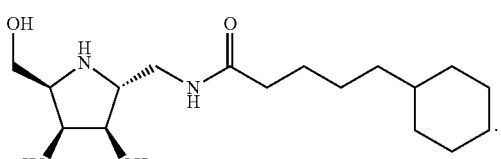
33

The details of one or more embodiments of this disclosure are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The accompanying drawings, which are incorporated in and constitute a part of the specification, illustrate various example systems, methods and other exemplified embodiments of various aspects of the invention. The present description will be better understood from the following detailed description read in light of the accompanying drawings, where.

DETAILED DESCRIPTION OF INVENTION

Figure 1:
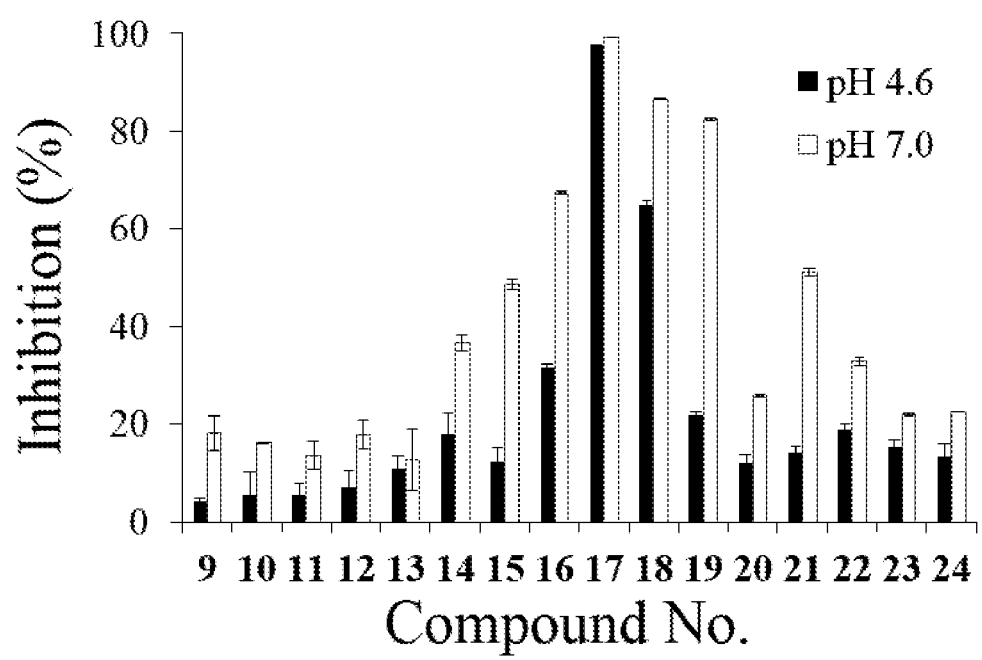
FIG. 1 illustrates the inhibitory profiles of compounds 9 to 24 toward α-Gal A at pH 4.6 or pH 7.0, in according to one embodiment of the present disclosure.

The detailed description provided below in connection with the appended drawings is intended as a description of the present disclosure and is not intended to represent the only forms in which the present disclosure may be constructed or utilized.

1. Definitions

Unless otherwise indicated, the term "amine" means a straight chain, branched and/or cyclic ("cycloalkyl") hydrocarbon having from 1 to 20 (e.g., 1 to 10, 1 to 9, 1 to 8, 1 to 7, 1 to 6, 1 to 5, 1 to 4, 1 to 3, 1 to 2, or 1) carbon atoms and including at least one amino group. Preferably, amine in the present discourse refers to lower alkyl amine, such as $C_{1-3}$ amine. Amines suitable for use in the present invention are primary or secondary amines, and unless otherwise specified, at least one of the hydrogen atom in the amino group is independently optionally substituted, i.e., unsubstituted (an "unsubstituted amine") or substituted (a "substituted amine") with one or more substituents. In certain embodiments, the amine is a methylene amine. In other embodiments, one of the hydrogen in the amino group of the methylene amine is substituted with an acyl group.

In a particular embodiment, the term "substituted," when used to describe a chemical structure or moiety, refers to a derivative of that structure or moiety wherein one or more of its hydrogen atoms is substituted with one or more of: acyl, alkoxy, alkyl, aryl, halo, haloalkyl, or hydroxyl.

The term "solvate" herein refers to a complex formed by the interaction of a compound (such as the compound of formula (I) of this invention) with surrounding solvent molecules, such as water, alcohols and other polar organic solvents. Alcohols include methanol, ethanol, n-propanol, isopropanol, n-butanol, isobutanol, and t-butanol. Alcohols also include polymerized alcohols such as polyalkylene glycols (e.g., polyethylene glycol, polypropylene glycol). The best-known and preferred solvent is typically water, and solvate compounds formed by solvation with water are termed hydrates.

Unless otherwise indicated, a "therapeutically effective amount" of a compound is an amount sufficient to provide a therapeutic benefit in the treatment or management of a disease or condition, or to delay or minimize one or more symptoms associated with the disease or condition. A therapeutically effective amount of a compound is an amount of therapeutic agent, alone or in combination with other therapies, which provides a therapeutic benefit in the treatment or management of the disease or condition. The term "effective amount" can encompass an amount that improves overall therapy, reduces or avoids symptoms or causes of a disease or condition, or enhances the therapeutic efficacy of another therapeutic agent.

The term "prophylactically effective amount" of a compound denotes the amount of the compound that is of sufficient quantity to prevent, delay onset, or reduce the risk of developing a disease or a condition in a subject.

The term "patient" and "subject" are used interchangeably in the present disclosure, and may be an animal or a human subject. The "FD patient" as used herein refers to an individual who has been diagnosed with FD and has a mutant form of α-Gal A that results in the inability of the enzyme to achieve a stable conformation under the conditions normally present in the endoplasmic reticulum (ER). The failure to achieve a stable confirmation in term results in substantial amount of α-Gal A being degraded, rather than being transported to lysosome. Non-limiting examples of α-Gal A mutation associated with FD include, but are not limited to, L32P, N34S, T41I, M51K, E59K, E66Q, I91T, A97V, R100K, R112C, R112H, F113L, T141L, A143T, G144V, A156V, L166V, D170V, C172Y, G183D, P205T, Y207C, Y207S, N215S, A228P, S235C, D244N, P259R, N263S, N264A, G272S, S276G, Q279E, Q279K, Q279H, M284T, W287C, I289F, M296I, M296V, L300P, R301Q, V316E, N320Y, G325D, G328A, R342Q, R356W, E358A, E358K, R363C, R363H, and P409A. According to preferred embodiments of the present disclosure, un-stabled α-Gal A comprises a mutation that is any of, R112H, P205T, Q279E, R301Q, R356W, or R363C.

Unless otherwise indicated, the terms "treat," "treating" and "treatment" contemplate an action that occurs while a patient is suffering from the specified disease or disorder, which reduces the severity of the disease or disorder, or one or more of its symptoms, or retards or slows the progression of the disease or disorder.

It should also be noted that if the stereochemistry of a structure or a portion of a structure is not indicated with, for example, bold or dashed lines, the structure or the portion of the structure is to be interpreted as encompassing all stereoisomers of it. Similarly, names of compounds having one or more chiral centers that do not specify the stereochemistry of those centers encompass pure stereoisomers and mixtures thereof. Moreover, any atom shown in a drawing with unsatisfied valences is assumed to be attached to enough hydrogen atoms to satisfy the valences.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The singular forms "a", "and", and "the" are used herein to include plural referents unless the context clearly dictates otherwise.

2. The Compounds of Present Invention

Compounds useful in this invention are stereoisomers of 1-aminodeoxy-DMDP (2,5-dideoxy-2,5-imino-d-mannitol, DMDP) (ADMDP), and derivatives thereof. The chemical structure of ADMDP comprises at least 4 asymmetric carbon atoms (i.e., chiral centers), thus ADMDP encompasses at least 16 stereoisomers. Inventors of the present invention developed a strategy to synthesize all 16 ADMDP stereoisomers (i.e., compounds 9 to 24), and derivatives thereof (i.e., compounds 28, 29, and 33-37), in accordance with the procedures described in working Example 1. The thus obtained ADMDP and/or its derivatives (i.e., compounds 9-24, 28, 29, and 33-37) were then subject to various assays for the evaluation of their applications as molecular chaperons in the treatment of fabry disease. These assays include at least, inhibition of α-Gal A, stabilization of recombinantα-Gal A, assistance in the folding of mutant α-Gal A, and their synergistic effects when co-administered with α-Gal A to lymphocytes derived from FD patient. According to data of the present disclosure, the compounds identified by afore-mentioned evaluation assays, i.e., the compound of formula (I), may be used as potential lead compounds for the development of medicaments for treating FD.

Accordingly, this invention encompasses the compound of formula (I), a salt, an ester or a solvate thereof for

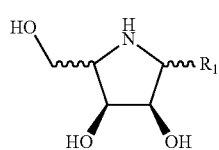
(I)

wherein:
$R_1$ is H or $C_{1-3}$ amine optionally substituted with $-COR_2$; and
$R_2$ is alkyl or alkene optionally substituted with cycloalkyl, or phenyl having at least one substituent selected from the group consisting of, halo, alkyl, haloalkyl, and alkoxyl.

Examples of the compound of formula (I) include, but are not limited to,

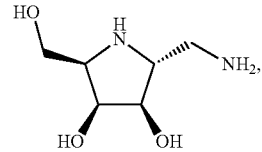
17

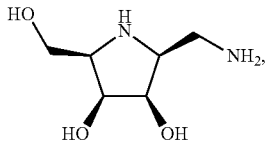
18

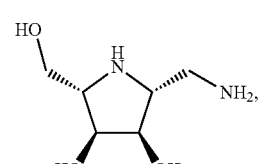
19

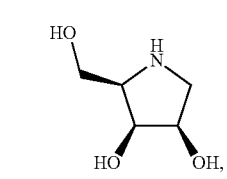
28

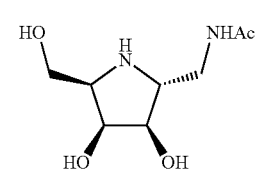
29

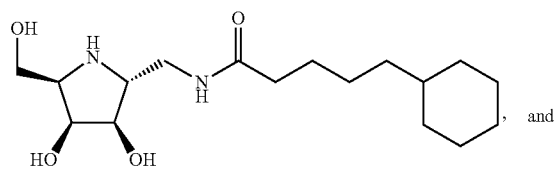
33 and

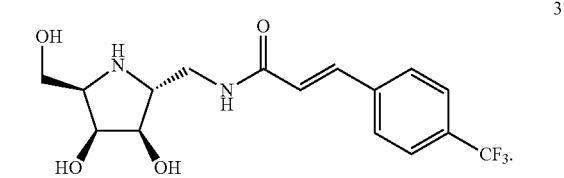
37

According to certain embodiments, the compound of the present disclosure has the structure of formula (I-1),

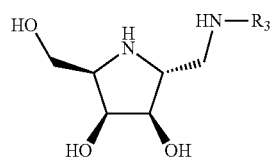
(I-1)

Wherein,
$R_3$ is H or $-COR_2$; and
$R_2$ is alkyl or alkene optionally substituted with cycloalkyl, or phenyl having at least one substituent selected from the group consisting of, halo, alkyl, haloalkyl, and alkoxyl.

In one preferred embodiment, the compound of formula (I-1) is

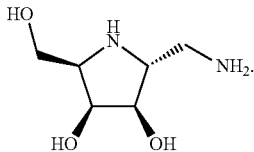   17

In another preferred embodiment, the compound of formula (I-1) is

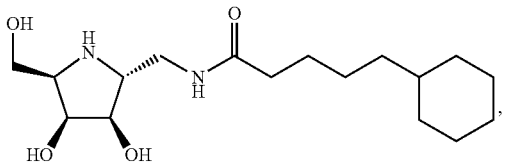   33

According to some embodiments of the preset disclosure, the compound of formula (I) is capable of suppressing α-GAL A activity.

According to other embodiments of the preset disclosure, the compound of formula (I) is a chaperon of a human lysosomal α-galactosidase A (α-Gal A) mutant. Specifically, the compound of formula (I) may assist the folding of a un-stabled α-Gal A or a mutant α-Gal A, which comprises a mutation that is any of, R112H, P205T, Q279E, R301Q, R356W, or R363C.

3. Method of Use

The present invention thus encompasses a method for the treatment or prophylaxis of a subject having or suspected of having FD. The method comprises the step of, administering a therapeutically or prophylactically effective amount of the compound of formula (I), a salt, an ester or a solvate thereof, to the subject, so as to ameliorate, alleviate, mitigate, and/or prevent the symptoms of FD. In some embodiments, the method further includes the step of administering to the subject a therapeutically effective amount of human α-Gal A, before, concurrently with, or after the administration of the compound of formula (I).

According to embodiments of the present disclosure, the compound of formula (I) is selected from the group consisting of,

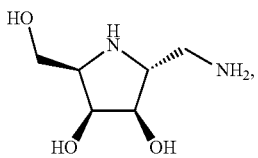   17

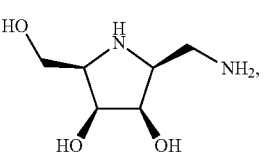   18

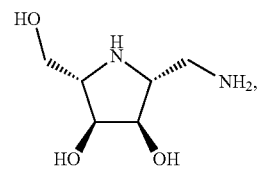   19

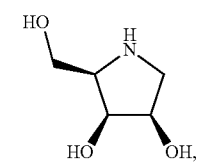   28

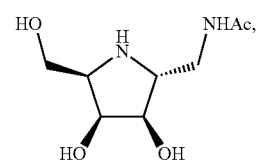   29

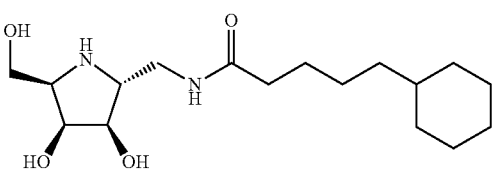   33 and

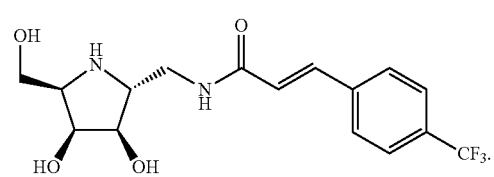   37

Preferably, the compound of formula (I) is compound 17, 33, or 37, a salt, an ester, and/or a solvate thereof. More preferably, the compound of formula (I) is compound 17. Still more preferably, the compound of formula (I) is compound 33.

According to embodiments of the present disclosure, the compound of formula (I) of the present disclosure is administered to the subject in the amount of about 0.001-500 g/day, such as 0.001, 0.01, 0.1, 1, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, and 500 g/day; preferably in the amount of about 0.05-450 g/day, such as 0.05, 0.5, 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, and 450 g/day; more preferably in the amount of about 5-400 mg/day, such as 5, 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, and 400 g/day.

The amount, route of administration and dosing schedule of the compound of formula (I) will depend upon factors such as the specific symptoms to be treated, prevented, or managed, and the age, sex and condition of the patient. The roles played by such factors are well known in the art, and may be accommodated by routine experimentation.

The compound of formula (I) may be combined with suitable pharmaceutical excipients or carriers and manufactured into medicaments (e.g., pharmaceutical composition or formulations) and administered to the FD patient via routes such as oral, parenteral, transdermal, topical, mucosal, and etc.

The compound of formula (I) may be present at a level of about 0.1% to 99% by weight, based on the total weight of the medicament. In some embodiments, the compound of formula (I) is present at a level of at least 1% by weight, based on the total weight of the medicament. In certain embodiments, the compound of formula (I) is present at a level of at least 5% by weight, based on the total weight of the medicament. In still other embodiments, the compound of formula (I) is present at a level of at least 10% by weight, based on the total weight of the medicament. In still yet other embodiments, the compound of formula (I) is present at a level of at least 25% by weight, based on the total weight of the medicament.

Certain medicaments are single unit dosage forms suitable for oral, mucosal (e.g., nasal, sublingual, vaginal, buccal, or rectal), parenteral (e.g., subcutaneous, intravenous, bolus injection, intramuscular, or intra-arterial), or transdermal administration to a patient. Examples of dosage forms include, but are not limited to: tablets; caplets; capsules, such as soft elastic gelatin capsules;

cachets; troches; lozenges; dispersions; suppositories; ointments; cataplasms (poultices); pastes; powders; dressings; creams; plasters; solutions; patches;

aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The medicament should suit the mode of administration. For example, oral administration requires enteric coatings to protect the compounds of this invention from degradation within the gastrointestinal tract. Similarly, a medicament may contain ingredients that facilitate delivery of the active ingredient(s) to the site of action. For example, compounds may be administered in liposomal formulations, in order to protect them from degradative enzymes, facilitate transport in circulatory system, and effect delivery across cell membranes to intracellular sites.

Similarly, poorly soluble compounds may be incorporated into liquid dosage forms (and dosage forms suitable for reconstitution) with the aid of solubilizing agents, emulsifiers and surfactants such as, but not limited to, cyclodextrins (e.g., $\alpha$-cyclodextrin or $\beta$-cyclodextrin), and non-aqueous solvents, such as, but not limited to, ethyl alcohol, isopropyl alcohol, ethyl carbonate, ethyl acetate, benzyl alcohol, benzyl benzoate, propylene glycol, 1,3-butylene glycol, dimethyl formamide, dimethyl sulfoxide (DMSO), biocompatible oils (e.g., cottonseed, groundnut, corn, germ, olive, castor, and sesame oils), glycerol, tetrahydrofurfuryl alcohol, polyethylene glycols, fatty acid esters of sorbitan, and mixtures thereof (e.g., DMSO:corn oil).

The composition, shape, and type of a medicament will vary depending on its use. For example, a medicament used in the acute treatment of a disease may contain larger amounts of one or more of the active ingredients it comprises than a medicament used in the chronic treatment of the same disease. Similarly, a parenteral medicament may contain smaller amounts of one or more of the active ingredients it comprises than an oral medicament used to treat the same disease. These and other ways in which specific medicament encompassed by this invention will vary from one another will be readily apparent to those skilled in the art. See, e.g., *Remington's Pharmaceutical Sciences,* 18th ed., Mack Publishing, Easton Pa. (1990).

3.1 Medicaments Suitable for Oral Administration

Medicaments comprising the compound of formula (I) of the present invention suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See, e.g., *Remington's Pharmaceutical Sciences,* 18th ed., Mack Publishing, Easton Pa. (1990).

Typical oral medicaments are prepared by combining the active ingredient(s) in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms. If desired, tablets can be coated by standard aqueous or non-aqueous techniques. Such dosage forms can be prepared by conventional methods of pharmacy. In general, medicaments are prepared by uniformly and intimately admixing the active ingredients with liquid carriers, finely divided solid carriers, or both, and then shaping the product into the desired presentation if necessary. Disintegrants may be incorporated in solid dosage forms to facility rapid dissolution. Lubricants may also be incorporated to facilitate the manufacture of dosage forms (e.g., tablets).

3.2 Medicaments Suitable for Parenteral Administration

Parenteral medicaments can be administered to patients by various routes including, but not limited to, subcutaneous, intravenous (including bolus injection), intramuscular, and intra-arterial. Because their administration typically bypasses patients' natural defenses against contaminants, parenteral dosage forms are specifically sterile or capable of being sterilized prior to administration to a patient. Examples of parenteral medicaments include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral medicaments of the invention are well known to those skilled in the art. Examples include, but are not limited to: water; aqueous vehicles such as, but not limited to, sodium chloride solution, Ringer's solution, and Dextrose; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

3.3 Medicaments Suitable for Transdermal, Topical and/or Mucosal Administration

Transdermal, topical, and mucosal medicaments include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences,* 18th eds., Mack Publishing, Easton Pa. (1990). Transdermal medicaments include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms are well known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with active ingredients of the invention. For example, penetration enhancers may be used to assist in delivering active ingredients to the tissue.

The pH of a medicament or dosage form, or of the tissue to which the medicament or dosage form is applied, may also be adjusted to improve delivery of one or more active ingredients. Similarly, the polarity of a solvent carrier, its ionic strength, or tonicity can be adjusted to improve delivery. Compounds such as stearates may also be added to medicaments or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition The present invention will now be described more specifically with reference to the following embodiments, which are provided for the purpose of demonstration rather than limitation. While they are typically of those that might be used, other procedures, methodologies, or techniques known to those skilled in the art may alternatively be used.

EXAMPLES

Materials and Methods
Cell Culture

Human lymphocytes (08C0058) and Fabry (GM04391) patient lymphocyte were maintained in RPMI-1640 (Gibco) supplemented with 15% FBS (fetal bovine serum; Invitrogen), 2 mM L-Glutamine and 1% penicillin/streptomycin (Gibco). COS-7 cells were cultured in DMEM (Dulbecco's modified Eagle's medium; Gibco) supplemented with 10% heat-inactivated FBS, 4 mM L-Glutamine and 1% penicillin/streptomycin. All cells were kept at 37° C. in a humidified 5% $CO_2$ incubator until used, and all cells used for biological evaluation were at 1-30 passage.

Cytotoxicity Assay Using Human Lymphocytes

Wild-type human lymphocytes (08C0058) were seeded in 96-well plates at a number of 50,000 cells/well. Medium were renewed after 24 hrs and test compounds were added to the culture medium to final concentrations of 10-200 μM. All compounds were dissolved in DMSO or $H_2O$ and control experiments were performed with DMSO. Cells were incubated at 37° C. in 5% $CO_2$ for 48-72 h. Then, 10λ alamarBlue was added to cells suspended in medium, and the mixture was incubated for additional 3-5 hrs at 37° C. in 5% $CO_2$. The number of viable cells was quantified and measured at 560 nm excitation and 590 nm emission.

In Vitro Stabilization of α-Gal A

An assessment of the ability of small molecules to stabilize α-Gal A against denaturation was performed by using Fabrazyme (rh-α-Gal A). Enzyme aliquots (20λ, pH 7.0) were incubated with 0, 0.5, 5 or 50 μM of compounds 17-19 on ice for 10 min. The samples were heated at 48° C. as a function of time in an attempt to heat-inactivate (denature) α-Gal A, and then the samples were diluted into three-fold volume of 0.1 M citric phosphate buffer (pH 4.6). The enzyme was immediately incubated with substrate (0.2 mM 4-methyllumbelliferyl α-D-galactoside) for 15 min at 37° C. before quenching with glycine buffer. Liberated 4-methylumbelliferone was measured (excitation 355 nm, emission 460 nm). Enzyme activity was reported relative to unheated enzyme.

Intracellular Activity Enhancement Assay for N215S Patient Lymphocytes

Fabry N215S patient lymphocyte (GM04391) were seeded in sterile clear-bottom 96-wells plate at a number of 20,000 cells/well and incubated at 37° C. and 5% $CO_2$ for 12-24 hrs. Then, the cells were cultured in the presence or absence of potent compounds for 4 days. The enzyme assay was performed: after being washed third times with PBS, the cells were homogenized in 50λ 0.1% triton X 100 in pH 4.6 buffer (citric phosphate) followed by 14,000 g centrifuge and 20λ of supernatant was incubated at 37° C. for 1 hr with 20λ of the substrate solution composed by 8 mM 4-methylumbelliferyl α-d-galactoside (4-MU-α-Gal) and 150 mM N-acetylgalactosamine using for inhibiting α-Gal B (N-acetylgalactosamidase) in 0.1 M citric phosphate buffer (pH 4.6) for enzyme assay. Stop solution (0.4 mol/L $K_2CO_3$, pH 10.6) was then added and fluorescence was read on a Victor plate reader at 355 nm excitation and 460 nm emission. Raw fluorescence counts were background subtracted, as defined by counts from substrate solution only. A MicroBCA Protein Assay Kit was used to determine protein concentration. 4-methylumbelliferone (4-MU) standard curve ranging from 0 μmol/L to 200 μmol/L was run in parallel day for conversion of fluorescence data to absolute α-Gal A activity expressed as nmol/mg protein per h. Relative α-Gal A activity was expressed as fold which was normalized to untreated enzyme activity.

Cloning of Lysosomal α-Galactosidase

A plasmid containing the full length cDNA of α-galactosidase A was obtained from RT-PCR. Amplification for cloning of wild-type human GLA gene was performed using KOD Hot Start DNA polymerase, with forward primer 5'-AGGTCGGATCCGACAATGCAGCTGAGGAACC-3' (SEQ ID NO: 1) and reverse primer 5'-GGTGGAATTCT-TAAAGTAAGT CTTTTAATGACATCTGCA-3' (SEQ ID NO: 2) introducing unique restriction sites for BamHI and EcoRI. 1.4 kb PCR product was observed through electrophoresis and could be identified by restriction enzyme. The amplicon was inserted into mammalian cloning vector, pJET2.1, to give constructed vector of mutagenesis.

Mutagenesis of Lysosomal α-Galactosidase A

Cloning vectors harbouring α-Gal A mutations were generated by site-directed PCR mutagenesis using the QuikChange Lightning Site-Directed Mutagenesis Kit. Nucleotide exchanges were individually introduced by PCR amplification with QuikChange Lightning Enzyme, the pJET2.1/GLA plasmid vector containing the wild type sequence was used as template and a 30-40-mer primer set shown in Table 1, with sense and antisense primers carrying one of the respective sequence modifications central to their length. Each mutant plasmid was identified by enzyme restriction and DNA electrophoresis, and sequenced by Genomics in Taiwan shown in FIG. 2. The pJET2.1/GLA was digested by restriction enzyme BamHI and EcoRI followed by further purification by electrophoresis.

The GLA gene was ligated into vector pcDNA3.1 and transformed into E. coli for amplification to give pcDNA3.1/GLA plasmid containing wild-type or mutated sequence for the use of transfection.

TABLE 1

Primer for site-directed PCR mutagenesis.

| primer | Sequence (5'→3') | GC% | N | mis% | Tm | SEQ ID NO |
|---|---|---|---|---|---|---|
| N215S-F | ggcccttcaaaagcccag ttatacagaaatccgacag | 47 | 38 | 2.6 | 66.6 | 3 |
| N215S-R | ctgtcggatttctgtataa ctgggcttttgaaagggcc | 47 | 38 | 2.6 | 66.6 | 4 |
| Q279E-F | tttggcctcagctggaatg agcaagtaactcagatggc | 51 | 39 | 2.5 | 68.7 | 5 |
| Q279E-R | ggccatctgagttacttgc tcattccagctgaggccaa a | 51 | 39 | 2.5 | 68.7 | 6 |
| R301Q-F | ttcatgtctaatgacctcc aacacatcagccctcaagc c | 49 | 39 | 2.5 | 67.6 | 7 |
| R301Q-R | ggcttgagggctgatgtgt tggaggtcattagacatga a | 49 | 39 | 2.5 | 67.6 | 8 |

Transient Transfection of COS-7 and Chaperone Assay

COS7 cells were seeded in 24-well plate at a number of $1\times10^5$ cells/well for 16-20 hrs and transiently transfected with expression plasmids containing human wild-type or mutant α-Gal cDNA using Mirus ILT-1 reagent. After 5-8 hr of incubation, the cells were exposed to fresh medium with or without compounds testing for chaperoning effect and incubated for 60 hr. Then, the cells were collected by 0.1% EDTA-trypsin and homogenized in 100λ 0.1% triton X100 in pH 4.6 buffer (citric phosphate) followed by 14,000 g centrifuge. α-Gal A activity in lysate was measured. Briefly, 10 Δ of supernatant was incubated at 37° C. for 1h with 10λ of the substrate solution composed by 8 mM 4-methylumbelliferyl α-D-galactoside (4-MU-α-Gal) and 150 mM N-acetylgalactosamine using for inhibiting α-Gal B (N-acetylgalactosamidase) in 0.1 M citric phosphate buffer (pH 4.6) for enzyme assay. Stop solution (0.4 mol/L $K_2CO_3$, pH 10.8) was then added and fluorescence was read on a Victor plate reader at 355 nm excitation and 460 nm emission. Raw fluorescence counts were background subtracted, as defined by counts from substrate solution only. A MicroBCA Protein Assay Kit was used to determine protein concentration. 4-methylumbelliferone (4-MU) standard curve ranging from 0 μmol/L to 200 μmol/L was run in parallel day for conversion of fluorescence data to absolute α-Gal A activity expressed as nmol/mg protein per h.

Glycosidase Activity Assay

The initial velocities of hydrolysis at room temperature or 37° C. were measured spectrophotometrically at various concentrations of p-nitrophenyl-glycopyranoside or 4-methylumbelliferyl-glycopyranoside at 405 nm absorbance or at 355 nm excitation and 460 nm emission using multi-detection reader (SpectraMax M5, Molecular Device). The data were fitted to the Michaelis-Menten equation using the GraphPad to determine the Km values and Vmax values. Enzymes from commercial source at 0.1 units per mL, Myozyme® (recombinant human acid α-glucosidase) at 20 nM, Cerezyme (recombinant human acid α-glucosidase) at 10 nM and α-galactosidase from human normal lymphocyte at 62 μg/ml were used to provide an ideal progression curve, and inhibitors were tested at 100 μM. The assays performed in a 96-well microtiter plate containing either sodium phosphate buffer (100 mM, pH 6.8) for α-glucosidase (Bacillus stearothermophilus) and α-galactosidase (Green coffee beans), or sodium citrate buffer (100 mM, pH 5.2) for Myozyme®, Cerezyme® and β-glucosidase (almonds) or sodium citrate buffer (100 mM, pH 4.5) for α-mannosidase (Jack bean) and α-galactosidase from human normal lymphocyte.

Thermal Stability Shift Assay

The stability of α-Gal A was assessed using a modified fluorescence thermal stability assay on a Rotor-Gene system in either neutral pH buffer (potassium phosphate, pH 7.0) or acidic pH buffer (citric phosphate, pH 4.6). Briefly, α-Gal A (2 μg) was combined with SYPRO Orange and various concentrations of 17, 28 and 29 in a final reaction volume of 20λ. A thermal gradient was applied to the plate at a rate of 1° C./minute, during which time the fluorescence of SYPRO Orange was continuously monitored. The fluorescence intensity at each temperature was normalized to the maximum fluorescence after complete thermal denaturation.

Alpha-Gal a Activity Assay in Patient Lymphocyte with Co-Administration of Fabrazyme and Compound 17

Fabry patient lymphocytes were seeded in sterile, clear-bottom, 96-well plates at 20000 cells/well, and incubated at 37° C., 5% $CO_2$ for 12-16 h. The cells were then incubated with fabrazyme (1 nmol/l) alone, or fabrazyme (1 nmol/l) and 17 (1, 10, 50 μmol/l) for 24 h. The cells were washed three times with growth medium, and then maintained in growth medium at 37° C., 5% $CO_2$ for 3 days.[9] The enzyme assay was performed: after being washed twice with PBS, the cells were homogenized in 50λ 0.1% triton X 100 in pH 4.6 buffer (citric phosphate) followed by 14000 g centrifuge and 20λ of supernatant was incubated at 37° C. for 1h with 20λ of the substrate solution composed by 8 mM 4-methylumbelliferyl α-D-galactoside (4-MU-α-Gal) and 150 mM N-acetylgalactosamine in 0.1 M citric phosphate buffer (pH 4.6) for enzyme assay. Stop solution (0.4 mol/L $K_2CO_3$, pH 10.8) was then added and fluorescence was read on a Victor plate reader (at 355 nm excitation and 460 nm emission). Raw fluorescence counts were background subtracted, as defined by counts from substrate solution only. A MicroBCA Protein Assay Kit was used to determine protein concentration. 4-methylumbelliferone (4-MU) standard curve ranging from 0 μmol/L to 200 μmol/L was run in parallel day for conversion of fluorescence data to absolute α-Gal A activity expressed as the nanomoles of 4-MU liberated per mg protein/hour (nmol/mg protein/hour). Relative α-Gal A activity was expressed as fold which was normalized to untreated enzyme activity.

Procedure of Preliminary Enzyme-Based Screening for Library

Libraries (20 μL) were diluted to give the final concentration of 20 μM, mixed with substrate 4-methylberiilyl α-D-galactopyranoside (20 μL) and recombinant human alpha-galactosidase (10 μL) in pH 4.6 buffer (50 μL), then assay was carried out at 37° C. for 15 min. Stop solution (0.4 mol/L $K_2CO_3$, pH 10.8) was then added and fluorescence was determined at 355 nm excitation and 460 nm emission. The control group was a mixture of HBTU, DIEA, acid libraries (in total 20 μL), substrate (20 μL), buffer (50 μL) and enzyme (10 μL) excluded the amide products. Blank was a solution of substrate (20 μL) and enzyme (10 μL) in pH 4.6 buffer (70 μL). Inhibition was performed as relative enzyme activity to control.

Procedure of Chasing Intracellular Activity Enhancement after Removal of Compounds for N215S Patient Lymphocyte Human lymphocytes with N215S mutant were seeded at a number of 20000 in 96-well plate (coster) for 12-16h. Increasing concentration (0-50 μM) of inhibitors was added and cells were incubated for 4 days. Then medium in 96 well was refreshed and cells were cultured for anther 0, 2, 4 days. After washing three times with PBS, 50λ lysis buffer (0.1 M sodium phosphate/citric acid buffer with 0.1% TX 100) was added to lymphocytes followed by pipetting and centrifugation at 4000 rpm for 1h. 20λ of cell lysate was added to 20λ of substrate solution including 8 mM 4MU-α-D-galactopyranoside and 150 mM N-acetyl-galactosamine in 0.1M sodium phosphate/citric acid buffer) and incubated at 37° C. for 1h. 40λ stop solution (sodium bicarbonate, pH 10.6) was added and fluorescence was read at 355 nm excitation and 460 nm emission. A 4-methylumbelliferone (4-MU) standard curve ranging from 0 nmol/L to 200 mol/L in 0.1M sodium phosphate/citric acid buffer (20λ) with 20λ 0.1 M sodium phosphate/citric acid buffer with 0.1% TX 100 was run for conversion of fluorescence data to absolute α-Gal A activity expressed as nmol/mg protein/hr. A MicroBCA Protein Assay Kit (Pierce, Rockford, Ill., USA) was used to determine protein concentration from 20λ of cell lysate.

Example 1 Preparation and Characterization of Compounds 9 to 37

1.1 Synthesis of Compounds 9 to 24

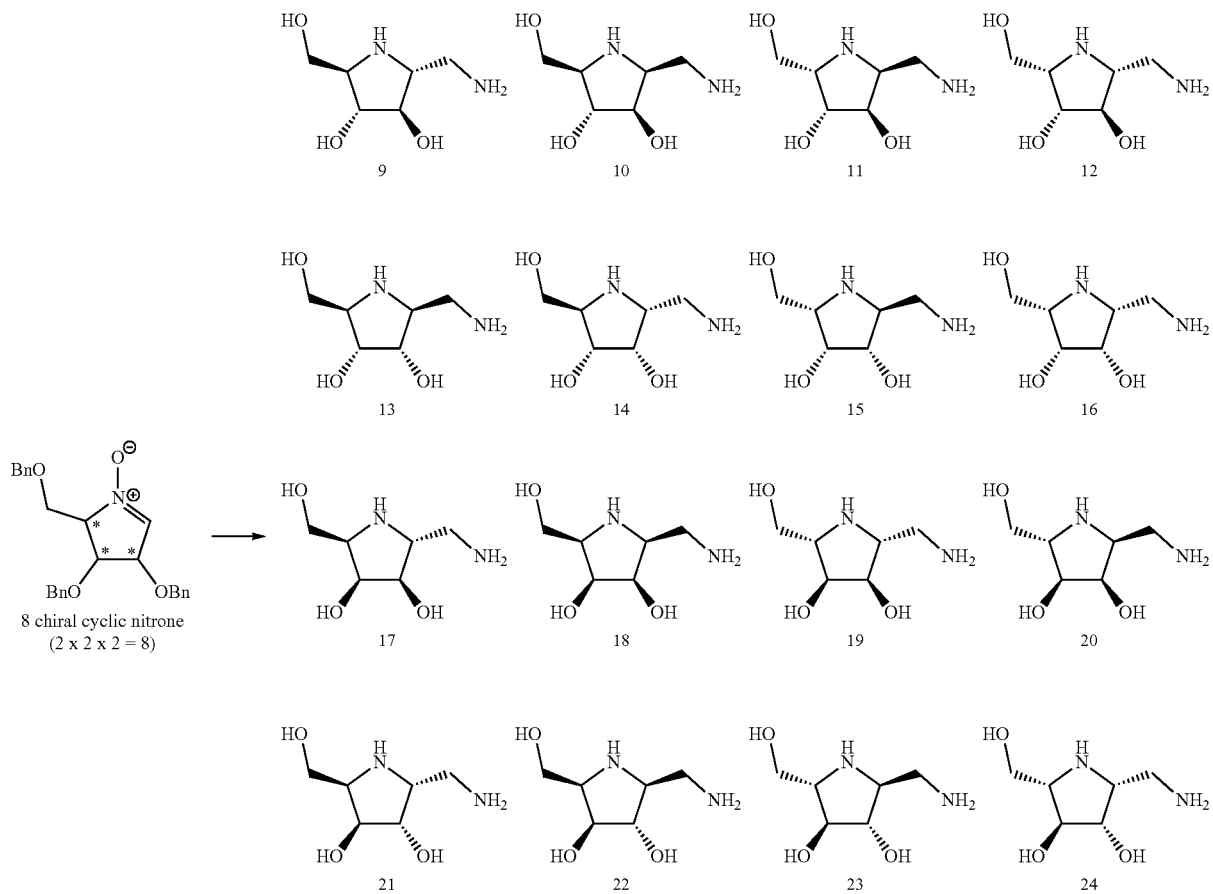

In this example, a total of 16 unnatural stereoisomers of amino-DMDP (or ADMDP), i.e., compounds 9 to 24, were prepared from eight corresponding pyrrolidine-type chiral tri-O-benzyl cyclic nitrones in accordance with the method described by Tsou et al (Tetrahedron 2009, 65, 93). Each cyclic nitrones acts as a precursor to generate two desired ADMDP-like products bearing the 2,3-cis and 2,3-trans configuration, dependent on the chemical transformations of the cyclic nitrones used. Scheme 1 provides a typical process for synthesizing compounds 17 and 18. Specifically, the highly diastereoselective nucleophilic addition of TMSCN to cyclic nitrone 25 in methanol at 50° C. gave the 2,3-trans isomer 26 as a major product (78%, dr≥20/1), which was then converted directly to 17 in good yield (60%) via a reductive-N-protection as well as O-Bn deprotection. On the other hand, inversion of the C-2 nitrile group in 26 was carried out via an elimination-reduction sequence to afford 27 (38% for two steps). Subsequently, global hydrogenolysis of 27 gave 18, the C2 epimer of 17, in 71% yield. All other isomers can be prepared in a range of 30-35% yield from the corresponding cyclic nitrones following the protocols similar to Scheme 1.

Scheme 1. A typical procedure for the preparation of 17 and 18.

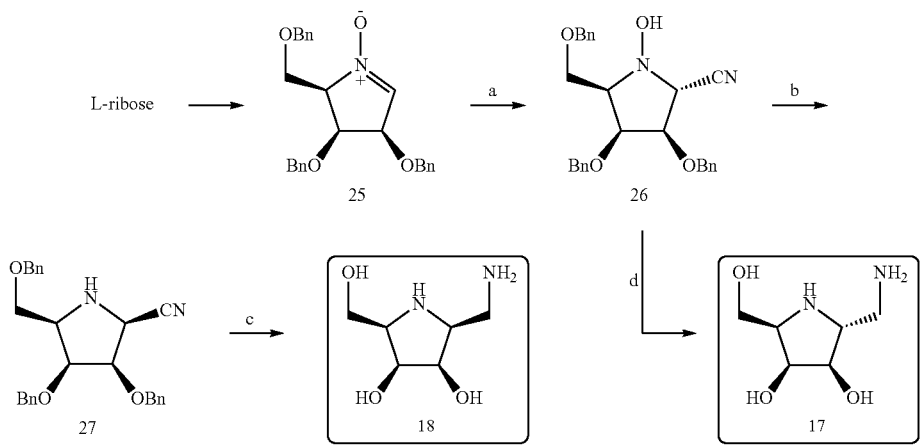

Conditions and reagents: (a) TMSCN, MeOH, 50° C., 10 h, 78%; (b) MsCl, Et₃N, THF, 20 min, 2) NaBH₄, MeOH/THF, 13 h, 38%; (c) Pd(OH)₂, conc. HCl, H₂, MeOH, 71%; (d) 1 Raney Ni, Boc₂O, H₂, MeOH, rt, 5 h, 2) conc. HCl, MeOH, reflux, 1 h; 3) Pd(OH)₂, conc. HCl, H₂, MeOH, rt, 10 h, 60% yield over three steps.

Preparation of 25

2,3,5-Tri-O-benzyl-L-ribofuranose (2.4 g, 5.8 mmol) was reacted with hydroxylamine hydrochloride (3.2 g, 46 mmol) in the presence of sodium methoxide (4.3 mL, 23 mmol, 5.4 M in methanol) in methanol (15 mL). The mixture was stirred at rt for 5 h and then the solvent was evaporated. The residue was extracted with EtOAc, washed with H₂O, dried over anhydrous MgSO₄, and concentrated. A mixture of the oxime residue, tert-butylchlorodiphenylsilane (TBDPSCl, 2.07 g, 7.5 mmol), and imidazole (0.6 g, 9.0 mmol) in CH₂Cl₂ (7.5 mL) was stirred at rt for 2 h and quenched with water (10 mL). The organic layer was washed with brine, dried over anhydrous MgSO₄, and concentrated. A mixture of silane residue was treated with methanesulfonyl chloride (0.67 mL, 8.7 mmol) in CH₂Cl₂ (15 mL) in the presence of triethylamine (1.2 mL, 8.7 mmol) at 0° C. for 3 h, the reaction mixture was quenched with water (15 mL). The organic layer was washed with brine, dried over anhydrous MgSO₄, and concentrated. The crude intermediate and TBAF (7.0 mL, 1 M in THF) in dry THF (15 mL) were stirred at rt for 30 min. The solvent was removed under vacuum and a mixture of residue, hydroxylamine hydrochloride (3.13 g, 45 mmol) and sodium bicarbonate (3.78 g, 45 mmol) in MeOH/H₂O (4/1, v/v, 58 mL) was stirred at 80° C. for 24 h. The solvent was removed under vacuum and the residue was purified by CC (50% EtOAc in hexanes, silica gel) to give cyclic nitrone 25 (1.09 g, 2.61 mmol, 45%) as a white solid; ¹H NMR (600 MHz, CDCl₃) δ4.09 (dd, 1H, J=3.3, 9.2 Hz), 4.15-4.19 (m, 2H), 4.37 (t, 1H, J=5.9 Hz), 4.53-4.60 (m, 4H), 4.68 (s, 2H), 4.70 (d, 1H, J=11.8 Hz), 6.91 (s, 1H), 7.24-7.35 (m, 15H); ¹³C NMR (150 MHz, CDCl₃) δ 137.7, 137.3, 137.2, 132.7, 128.5, 128.4, 128.3, 128.0, 127.9, 127.8, 127.7, 127.6, 127.5, 74.5, 74.0, 73.4, 73.0, 72.4, 66.5. HRMS calcd for [C₂₆H₂₇NO₄+Na]⁺ 440.1832, found 440.1843.

Preparation of 26

A mixture of compound 25 (420 mg, 1 mmol) and trimethylsilyl cyanide (320 μL, 2.5 mmol) in dry methanol (5 mL) was stirred at 50° C. for 10 h. The solvent was removed under vacuum and the residue was purified by CC (20% EtOAc in hexanes, silica gel) to give pure 26 (344 mg, 0.78 mmol, 78%) as a white solid; ¹H NMR (600 MHz, CDCl₃) δ3.57 (dd, 1H, J=6.8, 12.9 Hz), 3.69 (dd, 1H, J=6.8, 9.7 Hz), 3.76 (dd, 1H, J=6.8, 9.7 Hz), 4.25 (t, 1H, J=5.5, 5.4 Hz), 4.32 (d, 1H, J=5.7 Hz), 4.33 (t, 1H, J=5.5, 5.3 Hz), 4.47-4.53 (m, 3H), 4.63 (d, 1H, J=11.9 Hz), 4.68-4.73 (m, 2H), 7.22-7.35 (m, 15H); ¹³C NMR (150 MHz, CDCl₃) δ 141.6, 141.5, 140.7, 132.5, 132.3, 132.2, 132.1, 131.9, 131.8, 131.7, 131.6, 120.4, 84.1, 81.2, 81.0, 80.9, 79.8, 72.9, 71.3, 64.3. HRMS calcd for [C₂₇H₂₈N₂O₄+Na]⁺ 467.1941, found 467.1959.

Preparation of 17

A mixture of 26 (0.29 g, 0.65 mmol), Raney nickel (0.05 g), and di-tert-butyl dicarbonate (700 mg, 3.25 mmol) in dry methanol (3 mL) was stirred under a hydrogen atmosphere. After 5 h, the solvent was removed under vacuum and the residue was purified by CC (10% EtOAc in hexanes, silica gel) to give Boc-protected intermediate. A mixture of Boc-protected intermediate and 37% HCl (1 mL) in methanol (3 mL) was refluxed at 50° C. After 1 h, palladium hydroxide (50 mg) was added and the reaction mixture was also stirred under a hydrogen atmosphere for further 10 h at rt. The reaction mixture was filtered through Celite and the filtrate was concentrated, and purified by CC (25% aqueous NH₄OH (37%) in 1-propanol, silica gel) to give 17 (63.2 mg, 0.39 mmol, 60%) as a yellowish oil. ¹H NMR (600 MHz, D₂O) δ2.81 (dd, 1H, J=8.0, 13.0 Hz), 2.97 (dd, 1H, J=4.4, 13.0 Hz), 3.12-3.16 (m, 1H), 3.24 (d, 1H, J=3.6 Hz), 3.60 (dd, 1H, J=6.6, 11.2 Hz), 3.74 (dd, 1H, J=6.6, 11.2 Hz), 3.90 (dd, 1H, J=4.4, 8.0 Hz), 4.11 (s, 1H); ¹³C NMR (150 MHz, D₂O) δ 75.4, 71.9, 60.2, 59.8, 59.7, 43.1. HRMS calcd for [C₆H₁₄N₂O₃+H]⁺ 163.1077, found 163.1083.

Preparation of 27

Compound 26 (1.09 g, 2.27 mmol) was treated with methanesulfonyl chloride (280 μL, 3.4 mmol) in THF (10 mL) in the presence of triethylamine (680 μL, 4.54 mmol) for 20 min. The reaction was quenched with H₂O and extracted with EtOAc. The organic layer was dried over anhydrous MgSO₄ and concentrated. A mixture of the above residue and sodium borohydride (210 mg, 5.2 mmol) in MeOH/THF (1/1, v/v, 8 mL) was stirred in an ice-water bath for 13 h. The solvent was removed and the reaction mixture was extracted with EtOAc and washed with brine. The organic layer was dried over anhydrous MgSO₄, concentrated, and purified by CC (25% EtOAc in hexanes, silica gel) to give pure 27 (391 mg, 0.91 mmol, 38%) as a white solid. $^1$H NMR (600 MHz, CDCl$_3$) δ 3.41 (dd, 1H, J=6.2, 10.3 Hz), 3.59 (dd, 1H, J=7.3, 9.2 Hz), 3.72 (dd, 1H, J=6.2, 9.2 Hz), 4.02 (m, 2H), 4.19 (d, 1H, J=7.3 Hz), 4.45 (d, 1H, J=11.7 Hz), 4.50 (d, 1H, J=11.7 Hz), 4.60-4.65 (m, 2H), 4.70 (d, 1H, J=11.9 Hz), 4.95 (d, 1H, J=11.9 Hz), 7.24-7.40 (m, 15H); $^{13}$C NMR (150 MHz, CDCl$_3$) δ 138.3, 137.9, 137.0, 128.3, 128.1, 128.0, 127.8, 127.6, 127.5, 127.5, 127.4, 127.2, 119.2, 80.2, 76.6, 73.2, 73.1, 72.6, 70.1, 58.5, 48.5. HRMS calcd for [C$_{27}$H$_{28}$N$_2$O$_3$+H]$^+$ 429.2173, found 429.2181.

Preparation of 18

A mixture of 27 (69 mg, 0.16 mmol) and palladium hydroxide (200 mg) in methanol (1 mL) was stirred under a hydrogen atmosphere for 24 h. After filtration through a Celite, the filtrate was concentrated and purified by CC (11.1% aqueous NH$_4$OH (37%) in 1-propanol, silica gel) to afford 18 (18.5 mg, 0.11 mmol, 71%) as a yellowish solid. $^1$H NMR (600 MHz, D$_2$O) δ 3.45 (dd, 1H, J=5.8, 13.8 Hz), 3.59 (dd, 1H, J=6.7, 13.8 Hz), 3.77-3.80 (m, 1H), 3.91 (dd, 1H, J=8.4, 12.2 Hz), 3.99 (dd, 1H, J=4.9, 12.2 Hz), 4.06 (q, 1H, J=6.5 Hz), 4.46 (t, 1H, J=4.6 Hz), 4.62 (dd, 1H, J=4.3, 7.0 Hz); $^{13}$C NMR (150 MHz, D$_2$O) δ 70.3, 69.8, 61.9, 57.7, 56.0, 37.2. HRMS calcd for [C$_6$H$_{14}$N$_2$O$_3$+Na]$^+$ 185.0897, found 185.0901.

Typical Procedure for the Preparation of 19

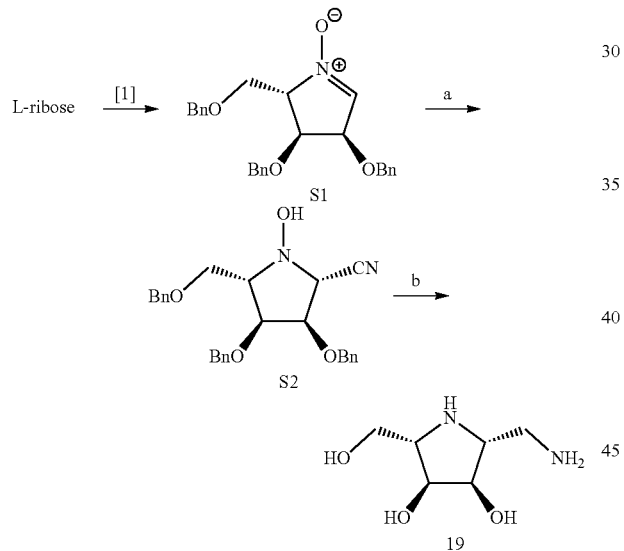

Conditions and reagents: [1] method described by Tsou et al., Tetrahedron 2009, 65, 93; (a) TMSCN, MeOH, 50° C., 7 h, 83%; (b) 1) Raney Ni, Boc$_2$O, H$_2$, MeOH, rt, 12 h; 2) conc. HCl, MeOH, reflux, 1 h; 3) Pd(OH)$_2$, conc. HCl, H$_2$, MeOH, 51% yield over three steps.

Preparation of S1

Following the same procedure as described for the preparation of 25 but iodination was carried out instead of mesylation. A mixture of silane residue (3.2 g, 4 mmol), triphenylphosphine (3.15 g, 12.0 mmol), imidazole (0.82 g, 12.0 mmol), and iodine (2.03 g, 8.0 mmol) in toluene (15 mL) was refluxed for 1 h, the reaction mixture was filtered, and washed with EtOAc. The organic layer was washed with brine, dried over anhydrous MgSO$_4$, and concentrated. The crude intermediate was dissolved in toluene (20 mL) and TBAF (4.8 mL, 1 M in THF) was added. After the reaction was refluxed at 110° C. for 30 min, the mixture was concentrated and purified by CC (25% EA in hexanes, silica gel) to give cyclic nitrone S1 (0.53 g, 1.27 mmol, 32%) as a syrup. $^1$H NMR (600 MHz, CDCl$_3$) δ 3.62 (dd, 1H, J=2.4, 10.6 Hz), 4.10-4.11 (m, 1H), 4.14 (dd, 1H, J=2.5, 10.7 Hz), 4.41 (d, 1H, J=11.9 Hz), 4.46 (dd, 1H, J=4.7, 6.0 Hz), 4.55 (dd, 2H, J=3.5, 11.7 Hz), 4.59-4.70 (m, 4H), 6.93 (s, 1H), 7.22-7.37 (m, 15H); $^{13}$C NMR (150 MHz, CDCl$_3$) δ 137.6, 137.4, 137.2, 133.4, 128.63 (×2), 128.58 (×2), 128.5 (×2), 128.21, 128.16 (×4), 128.1 (×2), 127.9, 127.7 (×2), 76.4, 75.4, 75.1, 73.5, 72.5, 72.1, 64.8. HRMS calcd for [C$_{26}$H$_{27}$NO$_4$+H]$^+$ 418.2013, found 418.2020.

Preparation of S2

The reaction was carried out as described above for 26 starting from S1 to give S2 as a white solid (83%). 1H NMR (600 MHz, CDCl$_3$) δ 3.31 (q, 1H, J=4.6 Hz), 3.49-3.54 (m, 2H), 3.83 (t, 1H, J=5.2 Hz), 4.06-4.11 (m, 2H), 4.44-4.53 (m, 3H), 4.58 (d, 1H, J=11.8 Hz), 4.63 (d, 1H, J=11.8 Hz), 4.68 (d, 1H, J=11.7 Hz), 7.24-7.35 (m, 15H); $^{13}$C NMR (150 MHz, CDCl$_3$) δ 137.5, 137.4, 136.7, 128.5 (×2), 128.41 (×2), 128.38 (×2), 128.2, 128.1 (×2), 128.0 (×2), 127.9, 127.83, 127.81 (×2), 118.5, 77.3, 75.1, 73.3, 72.7, 72.1, 71.9, 67.9, 61.8. HRMS calcd for [C$_{27}$H$_{28}$N$_2$O$_3$+H]$^+$ 445.2122, found 445.2130.

Preparation of 19

The reaction was carried out as described above for 17 starting from S2 to give 19 as a yellowish solid (51%). $^1$H NMR (600 MHz, D$_2$O) δ 2.75 (dd, 1H, J=7.6, 13.1 Hz), 2.93 (dd, 1H, J=5.1, 13.1 Hz), 3.07-3.11 (m, 2H), 3.59 (dd, 1H, J=5.8, 11.7 Hz), 3.67 (dd, 1H, J=4.7, 11.7 Hz), 3.76 (t, 1H, J=6.2 Hz), 3.86 (t, 1H, J=5.7 Hz); $^{13}$C NMR (150 MHz, D$_2$O) δ 73.5, 72.0, 63.6, 62.4, 62.3, 43.0. HRMS calcd for [C$_6$H$_{14}$N$_2$O$_3$+H]$^+$ 163.1077, found 163.1071.

Preparation of 9

The reaction was carried out as described above for starting from chiral cyclic nitrone to give 9 as a yellowish solid. (45%). $^1$H NMR (600 MHz, D$_2$O) δ 3.18 (dd, 2H, J=8.4, 13.3 Hz), 3.31 (dd, 1H, J=4.8, 13.3 Hz), 3.40-3.43 (m, 1H), 3.73 (dd, 1H, J=6.1, 11.9 Hz), 3.81 (dd, 1H, J=3.9, 12.1 Hz), 3.92-3.95 (m, 2H); $^{13}$C NMR (150 MHz, D$_2$O) δ 78.6, 76.4, 62.1, 60.5, 58.0, 41.3. HRMS calcd for [C$_6$H$_{14}$N$_2$O$_3$+H]$^+$ 163.1077, found 163.1071.

Preparation of 10

The reaction was carried out as described above for starting from chiral cyclic nitrone to give 10 as a yellowish solid. (25%). $^1$H NMR (600 MHz, D$_2$O) δ 3.09 (dd, 1H, J=6.3, 13.1 Hz), 3.13 (q, 1H, J=5.5 Hz), 3.24 (dd, 1H, J=6.0, 13.1 Hz), 3.59 (q, 1H, J=6.1 Hz), 3.64 (dd, 1H, J=6.5, 11.6 Hz), 3.74 (dd, 1H, J=4.5, 11.6 Hz), 3.90 (dd, 1H, J=3.8, 5.3 Hz), 4.20 (dd, 1H, J=3.8, 5.8 Hz); $^{13}$C NMR (150 MHz, D$_2$O) δ 77.9, 76.8, 64.0, 62.2, 55.9, 39.2. HRMS calcd for [C$_6$H$_{14}$N$_2$O+H]$^+$ 163.1077, found 163.1074.

Preparation of 11

The reaction was carried out as described above for starting from chiral cyclic nitrone to give 11 as a yellowish solid. (43%). $^1$H NMR (600 MHz, D$_2$O) δ 3.24 (dd, 1H, J=6.9, 13.8 Hz), 3.35 (dd, 1H, J=6.6, 13.8 Hz), 3.68 (dd, 1H, J=8.8, 12.1 Hz), 3.79 (dd, 1H, J=4.7, 12.1 Hz), 3.80-3.90 (m, 2H), 4.28 (d, 1H, J=3.6 Hz), 4.32 (d, 1H, J=3.6 Hz); $^{13}$C NMR (150 MHz, D$_2$O) δ 75.8 (×2), 61.8, 58.8, 57.3, 38.0. HRMS calcd for [C$_6$H$_{14}$N$_2$O+H]$^+$ 163.1077, found 163.1078.

Preparation of 12

The reaction was carried out as described above for starting from chiral cyclic nitrone to give 12 as a yellowish solid. (27%). $^1$H NMR (600 MHz, D$_2$O) δ 3.24 (dd, 1H, J=7.6, 13.3 Hz), 3.31 (dd, 1H, J=5.3, 13.3 Hz), 3.43-3.45 (m, 1H), 3.61 (dd, 1H, J=5.2, 12.2 Hz), 3.73 (dd, 1H, J=7.2, 11.5 Hz), 3.83 (dd, 1H, J=5.3, 11.5 Hz), 4.02 (t, 1H, J=3.2 Hz), 4.20 (dd, 1H, J=3.0, 4.9 Hz); $^{13}$C NMR (150 MHz, D$_2$O) δ 78.8, 75.6, 61.5, 60.8, 59.3, 41.0. HRMS calcd for [C$_6$H$_{14}$N$_2$O+H]$^+$ 163.1077, found 163.1069.

Preparation of 13

The reaction was carried out as described above for starting from chiral cyclic nitrone[1] to give 13 as a yellowish solid. (55%). $^1$H NMR (600 MHz, D$_2$O) δ 3.54 (m, 2H), 3.81 (dd, 1H, J=4.0, 9.0 Hz), 3.86 (m, 2H), 3.95 (dd, 1H, J=3.8, 12.6 Hz), 4.22-4.27 (m, 2H); $^{13}$C NMR (150 MHz, D$_2$O) δ 72.5, 70.2, 65.9, 58.8, 58.4, 38.65. HRMS calcd for [C$_6$H$_{14}$N$_2$O$_3$+H]$^+$ 163.1077, found 163.1078.

Preparation of 14

The reaction was carried out as described above for starting from chiral cyclic nitrone[1] to give 14 as a yellowish solid. (31%). $^1$H NMR (600 MHz, D$_2$O) δ 3.46 (dd, 1H, J=6.5, 13.8 Hz), 3.61 (dd, 1H, J=6.7, 13.8 Hz), 3.69-3.72 (m, 1H), 3.85 (dd, 1H, J=5.9, 12.7 Hz), 3.97-4.02 (m, 2H), 4.32 (dd, 1H, J=3.8, 8.7 Hz), 4.43 (t, 1H, J=3.5 Hz); $^{13}$C NMR (150 MHz, D$_2$O) δ 71.2, 70.1, 62.4, 57.9, 57.7, 36.1. HRMS calcd for [C$_6$H$_{14}$N$_2$O+H]$^+$ 163.1077, found 163.1073.

Preparation of 15

The reaction was carried out as described above for starting from chiral cyclic nitrone to give 15 as a yellowish solid. (47%). $^1$H NMR (600 MHz, D$_2$O) δ 3.11 (dd, 1H, J=8.5, 13.1 Hz), 3.24 (dd, 1H, J=4.8, 13.1 Hz), 3.35-3.41 (m, 2H), 3.68 (dd, 1H, J=7.0, 11.5 Hz), 3.82 (dd, 1H, J=6.1, 11.5 Hz), 4.03 (dd, 1H, J=4.0, 8.7 Hz), 4.17 (t, 1H, J=3.8 Hz); $^{13}$C NMR (150 MHz, D$_2$O) δ 75.4, 71.5, 60.3, 59.7, 57.7, 42.0. HRMS calcd for [C$_6$H$_{14}$N$_2$O$_3$+H]$^+$ 163.1077, found 163.1073.

Preparation of 16

The reaction was carried out as described above for starting from chiral cyclic nitrone to give 16 as a yellowish solid. (15%). $^1$H NMR (600 MHz, D$_2$O) δ 3.16 (dd, 1H, J=5.3, 11.6 Hz), 3.24 (dd, 1H, J=5.9, 13.5 Hz), 3.44 (d, 1H, J=5.2 Hz), 3.64-3.69 (m, 2H), 3.82 (dd, 1H, J=5.3, 11.5 Hz), 4.3 (t, 1H, J=4.7 Hz), 4.45 (dd, 1H, J=4.6, 7.2 Hz); $^{13}$C NMR (150 MHz, D$_2$O) δ 71.4, 70.7, 60.0, 55.0 (×2), 39.0. HRMS calcd for [C$_6$H$_{14}$N$_2$O+H]163.1077, found 163.1074.

Preparation of 20

The reaction was carried out as described above for starting from chiral cyclic nitrone to give 20 as a yellowish solid. (43%). $^1$H NMR (600 MHz, D$_2$O) δ 3.46 (dd, 1H, J=6.5, 13.8 Hz), 3.61 (dd, 1H, J=6.7, 13.8 Hz), 3.69-3.72 (m, 1H), 3.85 (dd, 1H, J=5.9, 12.7 Hz), 3.97-4.02 (m, 2H), 4.32 (dd, 1H, J=3.8, 8.7 Hz), 4.43 (t, 1H, J=3.5 Hz); $^{13}$C NMR (150 MHz, D$_2$O) δ 71.2, 70.1, 62.4, 57.9, 57.7, 36.1. HRMS calcd for [C$_6$H$_{14}$N$_2$O+H]$^+$ 163.1077, found 163.1073.

Preparation of 21.HCl

The reaction was carried out as described above for starting from chiral cyclic nitrone to give 21 as a yellowish solid. (36%). $^1$H NMR (600 MHz, D$_2$O) δ 3.48 (dd, 1H, J=6.9, 13.8 Hz), 3.57 (dd, 1H, J=6.6, 13.8 Hz), 3.90 (dd, 1H, J=8.8, 12.1 Hz), 3.98 (dd, 1H, J=4.7, 12.1 Hz), 4.03-4.06 (m, 1H), 4.14-4.17 (m, 1H), 4.39 (d, 1H, J=3.6 Hz), 4.41 (d, 1H, J=3.6 Hz); $^{13}$C NMR (150 MHz, D$_2$O) δ 74.6, 74.2, 63.7, 58.2, 57.3, 36.0. HRMS calcd for [C$_6$H$_{14}$N$_2$O+H]$^+$ 163.1077, found 163.1078.

Preparation of 22

The reaction was carried out as described above for starting from chiral cyclic nitrone to give 22 as a yellowish solid. (27%). $^1$H NMR (600 MHz, D$_2$O) δ 3.24 (dd, 1H, J=7.6, 13.3 Hz), 3.31 (dd, 1H, J=5.3, 13.3 Hz), 3.43-3.45 (m, 1H), 3.61 (dd, 1H, J=5.2, 12.2 Hz), 3.73 (dd, 1H, J=7.2, 11.5 Hz), 3.83 (dd, 1H, J=5.3, 11.5 Hz), 4.02 (t, 1H, J=3.2 Hz), 4.20 (dd, 1H, J=3.0, 4.9 Hz); $^{13}$C NMR (150 MHz, D$_2$O) δ 78.8, 75.6, 61.5, 60.8, 59.3, 41.0. HRMS calcd for [C$_6$H$_{14}$N$_2$O+H]$^+$ 163.1077, found 163.1069.

Preparation of 23

The reaction was carried out as described above for starting from chiral cyclic nitrone to give 23 as a yellowish solid. (46%). $^1$H NMR (600 MHz, D$_2$O) δ 3.03 (m, 2H), 3.18 (dd, 1H, J=4.3, 12.9 Hz), 3.24 (m, 1H), 3.64 (dd, 1H, J=5.7, 11.4 Hz), 3.71 (dd, 1H, J=3.4, 11.5 Hz), 3.78-3.83 (m, 2H); $^{13}$C NMR (150 MHz, D$_2$O) δ 79.2, 77.1, 61.7, 61.1, 57.9, 42.0. HRMS calcd for [C$_6$H$_{14}$N$_2$O$_3$+H]$^+$ 163.1077, found 163.1071.

Preparation of 24

The reaction was carried out as described above for starting from chiral cyclic nitrone to give 24 as a yellowish solid. (37%). $^1$H NMR (600 MHz, D$_2$O) δ 3.51 (dd, 1H, J=6.5, 13.8 Hz), 3.60 (dd, 1H, J=6.5, 13.8 Hz), 3.67-3.70 (m, 1H), 3.85 (dd, 1H, J=8.6, 12.1 Hz), 3.97 (dd, 1H, J=4.8, 12.1 Hz), 4.08-4.11 (m, 1H), 4.13 (s, 1H), 4.36 (s, 1H); $^{13}$C NMR (150 MHz, D$_2$O) δ 75.7, 74.7, 67.9, 59.3, 58.6, 35.6. HRMS calcd for [C6H14N2O+H]$^+$ 163.1077, found 163.1072.

1.2 Synthesis of Compounds 28 and 29

Compounds 28 and 29 were respectively prepared in accordance with procedures described in scheme 2. Specifically, 28 was prepared from cyclic nitrone 25 of scheme 1 via hydrogenolysis, whereas 29 was synthesized from 17 by selective acylation.

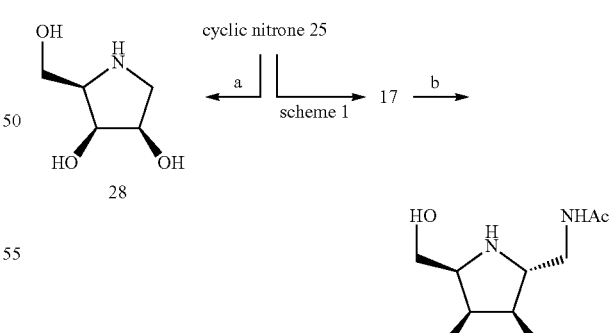

Scheme 2.

Conditions and reagents: (a) MeOH, Pd(OH)$_2$, H$_{2(g)}$, 79% (b) Ac$_2$O, MeOH/H$_2$O, rt, 4 h, 56%.

Preparation of 28

A mixture of 25 (81 mg, 0.19 mmol) and palladium hydroxide (30 mg) in methanol (1.5 mL) was stirred under a hydrogen atmosphere for 24 h. After filtration through Celite, the filtrate was concentrated and purified by CC (25% aqueous NH$_4$OH (37%) in 1-propanol, silica gel) to afford 28 (20.0 mg, 0.15 mmol, 79%) as a yellowish solid. $^1$H NMR (600 MHz, D$_2$O) δ 3.23 (dd, 1H, J=7.3, 12.1 Hz), 3.55 (dd, 1H, J=7.3, 12.1 Hz), 3.74-3.77 (m, 2H), 3.91 (dd, 1H, J=8.6, 12.2 Hz), 4.01 (dd, 1H, J=4.8, 12.2 Hz), 4.37 (t, 1H, J=4.2 Hz), 3.86 (td, 1H, J=4.1, 7.4 Hz); $^{13}$C NMR (150 MHz, D$_2$O) δ 70.0, 69.8, 62.4, 57.6, 47.0. HRMS calcd for [C$_5$H$_{11}$NO$_3$+H]$^+$ 134.0812, found 134.0813.

Preparation of 29

A mixture of 17 (10.0 mg, 0.06 mmol) and acetic anhydride (15.0 µL, 0.15 mmol) in solution H$_2$O/MeOH (1/3, v/v, 400 µL) was stirred at rt for 4 h. The reaction mixture was neutralized with Dowex 550A (OH$^-$) anion exchange resin. The mixture was filtered and washed with MeOH (2 mL). The filtrate was concentrated and the residue was purified by CC (12.5% aqueous NH$_4$OH (37%) in propanol, silica gel) to give 29 (6.9 mg, 0.03 mmol, 56%) as a yellow syrup. $^1$H NMR (600 MHz, D$_2$O) δ2.04 (s, 3H), 3.57 (dd, 1H, J=8.1, 15.8 Hz), 3.66 (m, 2H), 3.77 (m, 1H), 3.88 (dd, 1H, J=8.4, 12.0 Hz), 3.97 (dd, 1H, J=5.2, 12.0 Hz), 4.20 (dd, 1H, J=3.9, 8.9 Hz), 4.31 (t, 1H, J=3.5 Hz); $^{13}$C NMR (150 MHz, D$_2$O) δ 176.0, 72.7, 69.9, 61.8, 60.4, 57.6, 39.1, 21.6. HRMS calcd for [C$_8$H$_{16}$N$_2$O$_4$+H]$^+$ 205.1183, found 205.1184

1.3 Synthesis of Compounds 30 to 37

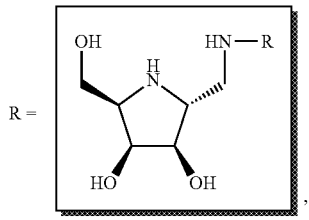

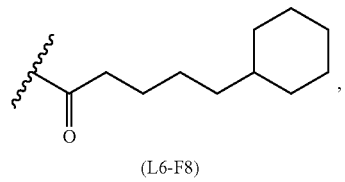

(L6-F8)

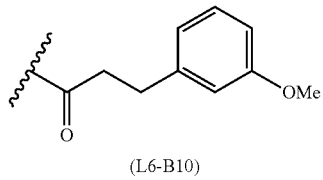

(L6-B10)

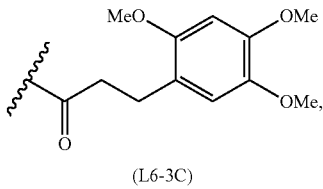

(L6-3C)

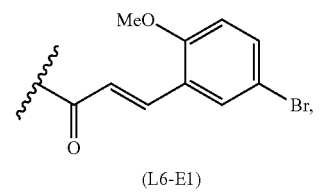

(L6-E1)

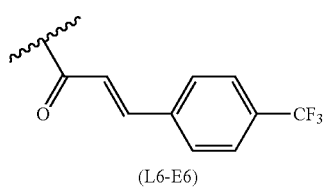

(L6-E6)

In this example, a 60-membered primary Library 5 and Library 6 were screed in accordance with procedures described in schemes 3 and 4; and the 5 potential hits (i.e., compounds 33 to 37) were then independently prepared in accordance with procedures exemplified in scheme 5 for the synthesis of compound 33.

Scheme 3.

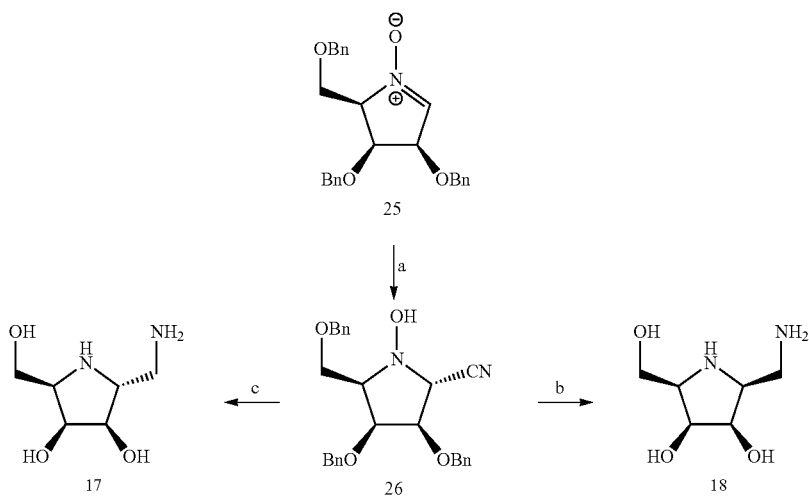

Conditions and reagents: (a) TMSCN, MeOH, 50° C., 10 h, 78%; (b) 1) MsCl, Et$_3$N, THF, 20 min, 2) NaBH$_4$, MeOH/THF, 13 h, 38%; 3) Pd(OH)$_2$, conc. HCl, H$_2$, MeOH, 71%; (c) 1 Raney Ni, Boc$_2$O, H$_2$, MeOH, rt, 5 h, 2) conc. HCl, MeOH, reflux, 1 h; 3) Pd(OH)$_2$, conc. HCl, H$_2$, MeOH, rt, 10 h, 60% yield over three steps.

Scheme 4.

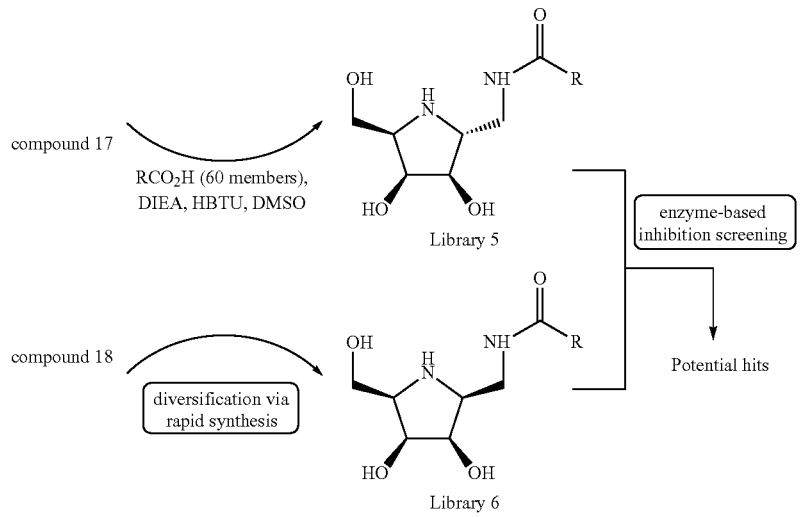

Compounds 17 and 18 having a common (3R,4S,5R) configuration (scheme 3) were used to generate two compound Libraries, i.e., Library 5 and Library 6 (scheme 4), in which parallel synthesis with a substituent diversity at the exo-amino methyl group of the compounds 17 and 18 was performed via an amide bond coupling with each constituent carboxylic acid of a randomly selected 60-membered acid by prior activation of carboxylic acids in the presence of HBTU (1.5 equiv), HOBt (1.5 equiv), and DIEA (3 equiv) in DMF. After 24 hrs, the reactions were analyzed and it was found that amine 17 and 18 had been completely consumed, and significant amount of desired products had formed. The 60-membered primary Library 5 (from compound 17) and Library 6 (from compound 18) were directly evaluated at 20 µM in α-Gal A enzyme-based inhibition assay without further purification (Scheme 4).

The primary screening result produced five hits that exhibited a qualified inhibition activity (>60% inhibition) (data not shown). In contrast, no promising inhibitor was found in Library 6 (data not shown). This finding indicated the configuration at the C2 position plays an important role for inhibition. In order to more carefully characterize these inhibitors, these five hits, compounds 33-37, were re-synthesized. Scheme 5 provides an exemplified procedure for the synthesis of compound 33.

Scheme 5.

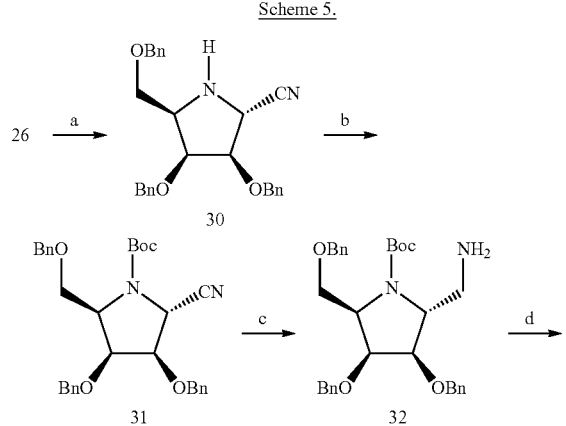

-continued

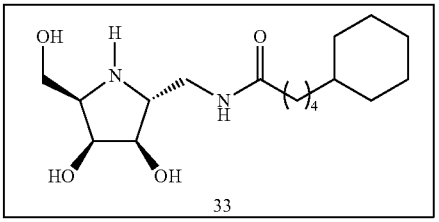

Reagents and conditions: (a) SmI$_2$, HOAc, THF, 0° C. to rt, 1 h, 70%; (b) Boc$_2$O, DIEA. CH$_2$Cl$_2$, 12 h; (c) Raney Ni, H$_2$, MeOH, 3 h, 50% over 2 steps (d) 1) RCOOH, EDC, DMAP, CH$_2$CL$_2$, 3 h, 2) Pd(OH)$_2$, H$_2$, HCl, 8 h, 50% over 2 steps.

Preparation of 25

2,3,5-Tri-O-benzyl-L-ribofuranose (2.4 g, 5.8 mmol) was reacted with hydroxylamine hydrochloride (3.2 g, 46 mmol) in the presence of sodium methoxide (4.3 mL, 23 mmol, 5.4 M in methanol) in methanol (15 mL). The mixture was stirred at rt for 5 h and then the solvent was evaporated. The residue was extracted with EtOAc, washed with H$_2$O, dried over anhydrous MgSO$_4$, and concentrated. A mixture of the oxime residue, tert-butylchlorodiphenylsilane (TBDPSCl, 2.07 g, 7.5 mmol), and imidazole (0.6 g, 9.0 mmol) in CH$_2$Cl$_2$ (7.5 mL) was stirred at rt for 2 h and quenched with water (10 mL). The organic layer was washed with brine, dried over anhydrous MgSO$_4$, and concentrated. A mixture of silane residue was treated with methanesulfonyl chloride (0.67 mL, 8.7 mmol) in CH$_2$Cl$_2$ (15 mL) in the presence of triethylamine (1.2 mL, 8.7 mmol) at 0° C. for 3 h, the reaction mixture was quenched with water (15 mL). The organic layer was washed with brine, dried over anhydrous MgSO$_4$, and concentrated. The crude intermediate and TBAF (7.0 mL, 1 M in THF) in dry THF (15 mL) were stirred at rt for 30 min. The solvent was removed under vacuum and a mixture of residue, hydroxylamine hydrochloride (3.13 g, 45 mmol) and sodium bicarbonate (3.78 g, 45 mmol) in MeOH/H$_2$O (4/1, v/v, 58 mL) was stirred at 80° C. for 24 h. The solvent was removed under vacuum and the residue was purified by CC (50% EtOAc in hexanes, silica gel) to give cyclic nitrone 25 (1.09 g, 2.61 mmol, 45%) as a white solid. $^1$H NMR (600 MHz, CDCl$_3$) δ4.09 (dd, 1H, J=3.3, 9.2 Hz), 4.15-4.19 (m, 2H), 4.37 (t, 1H, J=5.9 Hz), 4.53-4.60 (m, 4H), 4.68 (s, 2H), 4.70 (d, 1H, J=11.8 Hz), 6.91 (s, 1H), 7.24-7.35 (m, 15H). $^{13}$C NMR (150 MHz, CDCl$_3$) δ 137.7, 137.3, 137.2, 132.7, 128.5, 128.4, 128.3, 128.0, 127.9, 127.8, 127.7, 127.6, 127.5, 74.5, 74.0, 73.4, 73.0, 72.4, 66.5. HRMS calcd for $[C_{26}H_{27}NO_4+Na]^+$ 440.1832, found 440.1843.

Preparation of 26

A mixture of compound 25 (420 mg, 1 mmol) and trimethylsilyl cyanide (320 μL, 2.5 mmol) in dry methanol (5 mL) was stirred at 50° C. for 10 h. The solvent was removed under vacuum and the residue was purified by CC (20% EtOAc in hexanes, silica gel) to give pure 26 (344 mg, 0.78 mmol, 78%) as a white solid; $^1$H NMR (600 MHz, CDCl$_3$) δ3.57 (dd, 1H, J=6.8, 12.9 Hz), 3.69 (dd, 1H, J=6.8, 9.7 Hz), 3.76 (dd, 1H, J=6.8, 9.7 Hz), 4.25 (t, 1H, J=5.5, 5.4 Hz), 4.32 (d, 1H, J=5.7 Hz), 4.33 (t, 1H, J=5.5, 5.3 Hz), 4.47-4.53 (m, 3H), 4.63 (d, 1H, J=11.9 Hz), 4.68-4.73 (m, 2H), 7.22-7.35 (m, 15H); $^{13}$C NMR (150 MHz, CDCl$_3$) δ 141.6, 141.5, 140.7, 132.5, 132.3, 132.2, 132.1, 131.9, 131.8, 131.7, 131.6, 120.4, 84.1, 81.2, 81.0, 80.9, 79.8, 72.9, 71.3, 64.3. HRMS calcd for $[C_{27}H_{28}N_2O_4+Na]^+$ 467.1941, found 467.1959.

Preparation of 30

A mixture of 26 (800 mg, 1.8 mmol), 75 ml samarium(I) iodide in THF (0.1 M) and HOAc (2.2 ml) were stirred in THF for 1h at rt. After filtration through a celite pad, the solvent was removed and the reaction mixture was extracted with EtOAc and $Na_2S_2O_{3(aq)}$. The organic layers were dried with MgSO$_4$, concentrated, and purified by CC (25% EtOAc in hexanes, silica gel) to give pure product as a colorless oil (540 mg, 0.91 mmol, 70%). $^1$H NMR (600 MHz, CDCl$_3$) δ 3.55-3.58 (m, 2H), 3.65 (dd, 1H, J=9.2, 12.2 Hz), 4.07-4.09 (m, 2H), 4.26 (dd, 1H, J=4.1, 6.6 Hz), 4.51-4.53 (m, 2H), 4.58 (d, 1H, J=11.6 Hz), 4.65-4.68 (m, 2H), 4.77 (s, 1H, 11.6 Hz), 7.32-7.40 (m, 15H). $^{13}$C NMR (150 MHz, CDCl$_3$) δ 141.8, 141.7, 140.8, 132.5, 132.3, 132.2, 132.0, 131.8, 131.7, 131.7, 131.7, 131.6, 124.4, 87.5, 81.2, 81.0, 80.9, 80.8, 72.7, 62.9, 53.9. HRMS calcd for $[C_{27}H_{28}N_2O_3+H]^+$ 429.2173, found 429.2174.

Preparation of 32

A mixture of 30 (540 mg, 1.26 mmol), Boc$_2$O (550 mg) and triethylamine (0.17 ml) in DCM were stirred for 24h at room temperature. The reaction solution was concentrated and followed by reduction of cyanide group with Raney Ni and H$_2$(g) in methanol for 3h. The mixtures were concentrated, and purified by CC (6% MeOH in DCM, silica gel) to give pure product as a colorless oil (340 mg, 0.63 mmol, 50%)

$^1$H NMR (600 MHz, CDCl$_3$) δ 1.43 (d, 9H), 2.53 (dd, 1H, 8.5, J=17.9 Hz), 2.87-2.97 (m, 1H), 3.59 (d, 1H, J=8.9 Hz), 3.74-3.80 (m, 1H), 3.93 (d, 1H, J=3.8 Hz), 4.14-4.20 (m, 3H), 4.45-4.80 (m, 6H), 7.24-7.33 (m, 15H). $^{13}$C NMR (150 MHz, CDCl$_3$) δ 154.3, 138.5, 138.3, 138.2, 128.3, 128.2, 128.0, 127.8, 127.6, 127.5, 127.3, 127.2, 127.1, 79.9, 79.5, 77.7, 73.1, 72.3, 71.9, 70.2, 64.3, 58.3, 42.6, 28.4. HRMS calcd for $[C_{32}H_{41}N_2O_5+H]^+$ 533.3010, found 533.3015.

Preparation of 33

A mixture of 32 (33.3 mg, 0.0625 mmol), EDC*HCl (35.9 mg, 0.1875 mmol), 4-dimethylamnopyridine (7.64 mg, 0.0625 mmol) and cyclohexanepentanoic acid (17.27 mg, 0.0937 mmol) in CH$_2$Cl$_2$ was stirred at rt for 3h. The reaction was quenched with H$_2$O and extracted with CH$_2$Cl$_2$. The organic layer was dried over anhydrous MgSO$_4$ and concentrated. The residue was purified by CC (33% EtOAc in hexanes, silica gel) to give amide intermediate. A mixture of amide intermediate and 37% HCl in methanol was refluxed at 50° C. After 1 h, palladium hydroxide (50 mg) was added and the reaction mixture was also stirred under a hydrogen atmosphere for further 10 h at rt. The reaction mixture was filtered through Celite and the filtrate was concentrated, and purified by CC (4.5% H$_2$O and 28% MeOH in CHCl$_3$, silica gel) to give 33 (9.87 mg, 0.03 mmol, 48% yield) as a yellowish oil. $^1$H NMR (600 MHz, D$_2$O) δ 1.04-1.24 (m, 11H), 1.49-1.63 (m, 6H), 2.18 (s, 2H), 3.09 (s, 1H), 3.22-3.24 (m, 2H), 3.35 (d, 1H, J=11.6 Hz), 3.52-3.55 (m, 1H), 3.70-3.67 (m, 1H), 3.82 (s, 1H), 4.08 (s, 1H); $^{13}$C NMR (150 MHz, D$_2$O) δ 176.4, 75.2, 71.9, 60.6, 59.9, 59.7, 41.7, 37.4, 37.1, 36.0, 33.2, 26.6, 26.4, 26.3, 25.9. HRMS calcd for $[C_{17}H_{32}N_2O_4+H]^+$ 329.2435, found 329.2435.

Preparation of 34

A mixture of 32 (53.9 mg, 0.1 mmol), EDC•HCl (57.5 mg, 0.3 mmol), 4-dimethylaminopyridine (12.2 mg, 0.1 mmol) and 3-(3-methoxyphenyl)-propionic acid (27 mg, 0.15 mmol) in CH$_2$Cl$_2$ was stirred at rt for 3h. The reaction was quenched with H$_2$O and extracted with CH$_2$Cl$_2$. The organic layer was dried over anhydrous MgSO$_4$ and concentrated. The residue was purified by CC (33% EtOAc in hexanes, silica gel) to give amide intermediate. A mixture of amide intermediate and 37% HCl in methanol was refluxed at 50° C. After 1 h, palladium hydroxide (50 mg) was added and the reaction mixture was also stirred under a hydrogen atmosphere for further 10 h at rt. The reaction mixture was filtered through Celite and the filtrate was concentrated, and purified by CC (4.5% H$_2$O and 28% MeOH in CHCl$_3$, silica gel) to give 34 (14.52 mg, 0.047 mmol, 47.1% yield) as a colorless oil. $^1$H NMR (600 MHz, D$_2$O) δ 263-2.70 (m, 2H), 2.96 (t, 2H), 3.03 (m, 1H), 3.19 (s, 1H), 3.32 (dd, 1H, J=6.0, 14.6 Hz), 3.45 (dd, 1H, J=3.3, 14.6 Hz), 3.58 (dd, 1H, J=4.0, 8.7 Hz), 3.64 (dd, 1H, J=7.1, 11.2 Hz), 3.77 (dd, J=6.0, 11.2 Hz), 3.86 (s, 3H), 4.03 (t, 1H, J=3.3 Hz), 6.91-6.95 (m, 3H), 7.35 (t, 1H, J=7.5 Hz); $^{13}$C NMR (150 MHz, D$_2$O) δ 176.5, 158.9, 142.2, 129.9, 121.4, 121.2, 114.2, 111.9, 73.5, 71.3, 59.9, 59.7, 55.2, 40.0, 36.8, 31.1. HRMS calcd for $[C_{16}H_{24}N_2O_5+H]^+$ 325.1763, found 325.1764.

Preparation of 35

A mixture of 32 (40.1 mg, 0.075 mmol), EDC•HCl (43 mg, 0.225 mmol), 4-dimethylaminpyridine (9.16 mg, 0.075 mmol) and 3-(2, 4, 5-trimethoxy-phenyl)-propionic acid (27 mg, 0.1125 mmol) in CH$_2$Cl$_2$ was stirred at rt for 3h. The reaction was quenched with H$_2$O and extracted with CH$_2$Cl$_2$. The organic layer was dried over anhydrous MgSO$_4$ and concentrated. The residue was purified by CC (33% EtOAc in hexanes, silica gel) to give amide intermediate. A mixture of amide intermediate and 37% HCl in methanol was refluxed at 50° C. After 1 h, palladium hydroxide (50 mg) was added and the reaction mixture was also stirred under a hydrogen atmosphere for further 10 h at rt. The reaction mixture was filtered through Celite and the filtrate was concentrated, and purified by CC (4.5% H$_2$O and 28% MeOH in CHCl$_3$, silica gel) to give 35 (15.08 mg, 0.039 mmol, 52% yield) as a yellowish solid. $^1$H NMR (600

MHz, D$_2$O) δ 2.49-2.54 (m, 1H), 2.55-2.60 (m, 1H), 2.77-2.83 (m, 2H), 3.06 (t, 1H, J=7.6 Hz), 3.22-3.37 (m, 2H), 3.47 (d, 1H, J=12.9 Hz), 3.63 (dd, 1H, J=3.5, 8.3 Hz), 3.68 (dd, 1H, J=8.3 Hz, 11.6 Hz), 3.74 (s, 3H), 3.75 (d, 1H, J=5.7 Hz), 3.77 (s, 3H), 3.79 (s, 3H), 3.97 (t, 1H, J=3.5 Hz), 6.70 (s, 1H), 6.81 (s, 1H); $^{13}$C NMR (150 MHz, D$_2$O) δ 177.6, 151.7, 147.5, 141.9, 120.2, 114.5, 98.8, 72.5, 70.4, 61.2, 60.2, 58.3, 56.7, 56.4, 55.9, 39.0, 35.5, 25.5. HRMS calcd for [C$_{18}$H$_{28}$N$_2$ O7+H]$^+$ 385.1975, found 385.1978.

Preparation of 37

A mixture of 32 (35 mg, 0.0657 mmol), EDC·HCl (37.8 mg, 0.197 mmol), 4-dimethylaminopyridine (8.03 mg, 0.0657 mmol) and trans-4-(trifluoro-methyl)cinnamic acid (21.3 mg, 0.131 mmol) in CH$_2$Cl$_2$ was stirred at rt for 3h. The reaction was quenched with H$_2$O and extracted with CH$_2$Cl$_2$. The organic layer was dried over anhydrous MgSO$_4$ and concentrated. The residue was purified by CC (33% EtOAc in hexanes, silica gel) to give amide intermediate. A mixture of amide intermediate and BBr$_3$ (32λ) in CH$_2$Cl$_2$ was stir at −78° C. for 2h. The reaction mixture was quenched by EtOH and concentrated, and purified by CC (4.5% H$_2$O and 28% MeOH in CHCl$_3$, silica gel) to give 37 (15.24 mg, 0.0423 mmol, 64.4% yield) as a yellowish solid. $^1$H NMR (600 MHz, D$_2$O) δ 3.44 (d, 1H, J=4.6 Hz), 3.51-3.58 (m, 2H), 3.70 (dd, J=1H, 4.6, 13.2 Hz), 3.75 (dd, 1H, J=7.2, 11.3 Hz), 3.88 (dd, 1H, J=6.2, 11.3 Hz), 4.10 (dd, 1H, J=3.9, 8.4 Hz), 4.26 (t, 1H, J=3.4, 3.4 Hz), 6.75 (d, 1H, J=15.8 Hz), 7.58 (d, 1H, J=15.8 Hz), 7.76 (s, 4H); $^{13}$C NMR (150 MHz, D$_2$O) δ 169.0, 140.1, 137.9, 128.3, 125.8, 122.1, 74.5, 71.3, 60.3, 59.9, 59.5, 41.2. HRMS calcd for [C$_{16}$H$_{19}$F$_3$N$_2$O$_4$+H]$^+$ 361.1380, found 361.1370.

1.4 Characterization of Compounds 9 to 24

In this example, the inhibitory activities of compounds 9 to 24 (at a concentration of 50 uM) against α-Gal A were respectively evaluated at pH 4.6 and 7.0, at which conditions chemical chaperone is regarded as tightly bind to the enzyme in the ER at neutral pH 7.0, but would be released at the lysosome at acidic pH 4.6. Results are depicted in FIG. 1.

As evident from FIG. 1, among the 16 compounds (i.e., compounds 9 to 24) that were tested, only compounds 17 and 18 exhibited the inhibitory activity more than 60% at pH 4.6. This finding suggests that the (3R,4S,5R) configuration pattern of 17 and 18 might play a critical role for the inhibitory potency against α-Gal A. Isomer 19, which possesses the (2R,3R,4S,5S) configuration, exhibited poor inhibitory potency at pH 4.6 but good inhibitory potency at pH 7.0. Other isomers had weak or no inhibition activity against α-Gal A in vitro. In addition, compounds 17-19 were further studied of their inhibition activities, and the results are provided in Table 2.

TABLE 2

| Compound | IC$_{50}$ (μM)[a] | |
|---|---|---|
| | pH 4.6 | pH 7.0 |
| 17 | 0.67 ± 0.002 | 0.053 ± 0.004 |
| 18 | 34.2 ± 1.0 | 10.6 ± 0.9 |
| 19 | 266 ± 2 | 14 ± 1 |

[a]IC$_{50}$ values were measured in triplicate experiments.

The inhibitory potency of 17 increased by about 13-fold from pH 4.6 (IC$_{50}$=0.67 μM) to pH 7.0 (IC$_{50}$=0.053 μM). This finding indicated that under the in vitro mimic conditions 17 possessed a favorable character to tightly bind to the defective α-Gal A enzyme in the ER (neutral pH) but it became a weaker binder at lysosome (acid pH). Likewise, the inhibition potency of 19 was about 19-fold higher at neutral than at acidic pH. By contrast, the inhibition potency of 18 was only about 3.2-fold higher at neutral (pH 7.0) than at acidic conditions (pH 4.6). Compound 17 was 200 times more potent than that of 18, and 264 times more potent than that of 19 at pH 7.0. Notably, the inhibitory activity of 18 was less potent than that of 17, suggesting the orientation of the C2-aminomethyl moiety would significantly influence the inhibitory activity.

1.5 Characterization of Compounds 33 to 37

The inhibitory activities of compounds 33 to 37 (at a concentration of 50 uM) against α-Gal A were also respectively evaluated at pH 4.6 and 7.0. Results are summarized in Table 3.

At the neutral pH, except compound 34, compounds 33, and 35-37, respectively exhibited in vitro rh-α-Gal A inhibition activity in the low micromolar range. Further, all compounds exhibited lower inhibition potency at pH 4.6. Their inhibition activities were weaker than the two reference compounds, DGJ (IC$_{50}$=0.013 μM) and DIA (IC$_{50}$=0.75 μM).

TABLE 3

| Compound | IC$_{50}$ (μM)[a] | |
|---|---|---|
| | pH 4.6[c] | pH 7.0[c] |
| 33 | 10.4 ± 2 | 2.1 ± 0.05 |
| 34 | 19.1 ± 2 | 13 ± 0.1 |
| 35 | 30.4 ± 4 | 7.7 ± 0.2 |
| 36 | 32.8 ± 4 | 3 ± 0.7 |
| 37 | 5.0 ± 0.7 | 1.1 ± 0.01 |
| DGJ[b] | 0.042 | 0.013 ± 0.00007 |
| DIA[b] | 1.0 ± 0.1 | 0.75 ± 0.09 |

[a]IC$_{50}$ values were measured in triplicate experiments.
[b]reference compound for comparison purpose.
[c]4MU-α-galactopyranoside as a substrate for this assay, Km = 0.3 mM at pH 4.6 and 2.4 mM at pH 7.0.

Example 2 Characterization of Chaperon Effects of Compounds 17, 33, and 37

Figure 2:
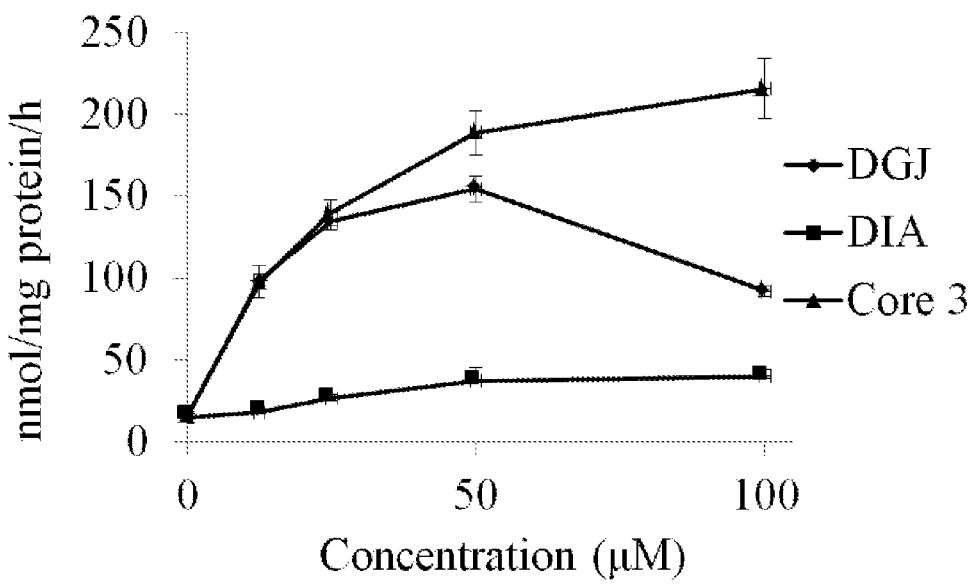
FIG. 2 depicts the chaperon effects of (a) compound 17, and (b) compound 33 or 37 toward human lymphocyte cell line N215S in according to one embodiment of the present disclosure.
Figure 2:
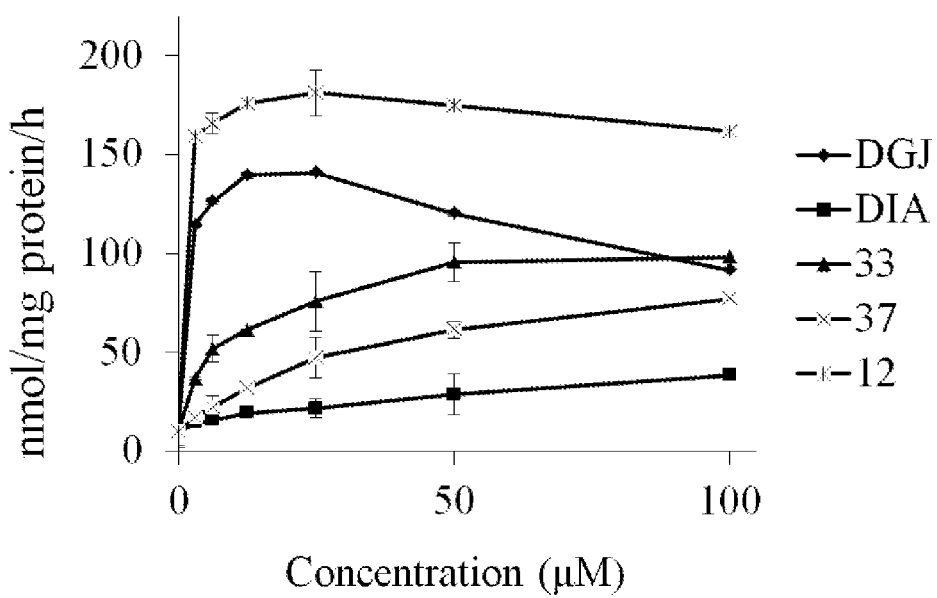

Based on the finding in example 1, compounds 17, 33, and 37 were chose for further studies, particularly for their respective efficacy as a molecular chaperon toward mutatedα-Gal A. Specifically, compound 17, 33 or 37 was subject to chemical chaperoning study toward FD patient cell lines N215S with certain mis-sense mutations, and results are illustrated in FIG. 2.

Surprisingly, compound 17 was able to enhance the mutant α-Gal A activity in a wide range of concentrations (from 0 to 100 μM). The addition of any of the compounds 17, 33, and 37 (100 μM) to N215S patient lymphocytes led to significant increases in α-Gal A activity (more than 10- and 18-folds increases for compounds 17 and 33, respectively), as compared with that of the control untreated cells (FIG. 2). Further, the chaperoning effect of 17 or 33 was better than that of DGJ or DIA. Specifically, the chaperoning effect of 33 was about 4-fold more potent than that of DGJ at the same concentration (25 μM), and about 13-fold more potent than that of DIA at the same concentration (100 μM).

Figure 3:
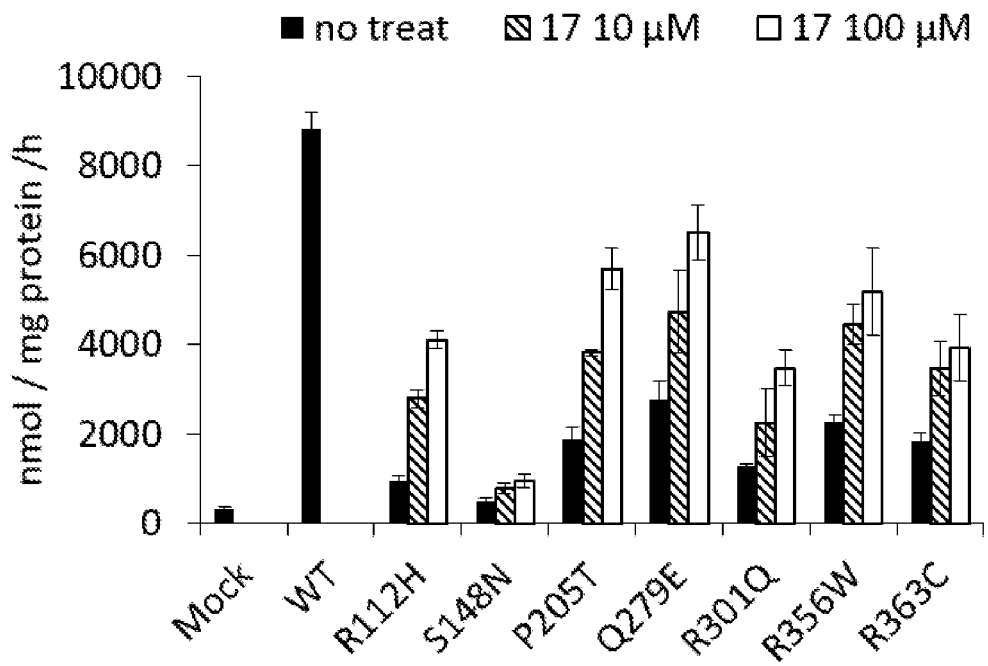
FIG. 3 illustrates the chaperon effects of (a) compound 17 and (b) compound 33 on rh-α-Gal A mutants in according to one embodiment of the present disclosure.
Figure 3:
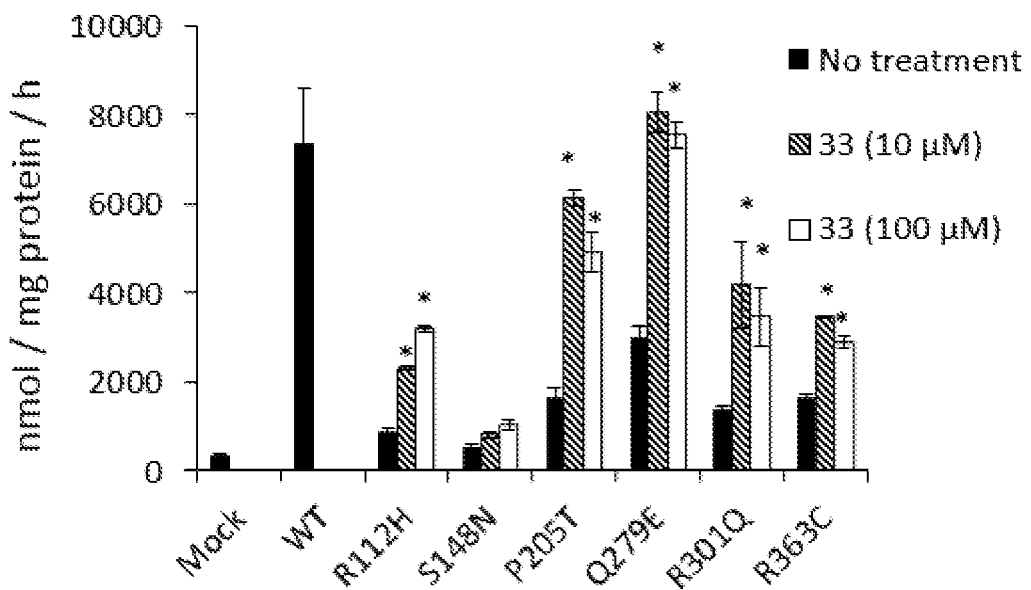

The effects of compounds 17 and 33 on other mis-sense α-Gal A mutants, which included R112H, S148N, P205T, Q279E, R310Q, R356W, and R363C, were respectively investigated, and results are summarized in FIG. 3. The data in FIG. 3 indicated that compound 17 exhibited satisfactory chaperoning activity toward these mutants except S148N, in which the activities of the deficient α-Gal As were respectively enhanced with the addition of compound 17 (at the concentration of 10 or 100 μM). Similar results were also found for compound 33, which exhibited satisfactory chaperoning activity toward these mutants except S148N in COS7 cells.

The inhibitory potency and selectivity of 17 was also examined towards a panel of glycosidases, including α-glucosidases, β-glucosidase, α-galactosidase, human β-galactosidase, recombinant human acid β-glucosidase (rh-GCase), and recombinant human acid α-glucosidase (rh-GAA) (data not shown), in which DGJ was used as a reference compound. It was found that compound 17 was a potent inhibitor against human lysosomal α-Gal A but exhibited low inhibitory activities against other glycosidases including human lysosomal GCase, rh-GAA, and β-galactosidase (from lysed human lymphocytes). Notably, compound 17 exhibited 8-fold less inhibitory activity against β-galactosidase than that of the positive control, 1-deoxygalactonojirimycin (DGJ). Presumably, compound 17 might have much less influence to the cellular lysosomal β-galactosidase activity.

As to the inhibitory potency and selectivity of 33, it was tested against a panel of glycosidases, including α-glucosidases from *Bacillus stearothermophilus*, β-glucosidase from almonds, β-mannosidase from Helix, α-mannosidase from Jack beans, α-galactosidase from coffee beans, recombinant human α-Gal A, and β-galactosidase from human lysate. Results are presented in Table 4.

TABLE 4

| Enzyme | Inhibition activity[a] (%) |
|---|---|
| α-glucosidase[b] | No inhibition |
| β-glucosidase[c] | No inhibition |
| β-mannosidase[d] | No inhibition |
| α-mannosidase[e] | 36 |
| α-galactosidase[f] | 94 |
| rh-α-Gal A[g] | 97 |
| β-galactosidase[h] | No inhibition |

[a]inhibitors were tested at 100 μM;
[b]from *Bacillus stearothermophilus*;
[c]from Almonds;
[d]from Helix;
[e]from Jack beans;
[f]from coffee beans;
[g]recombinant human α-Gal A;
[h]from human lysate.

Compound 33 (100 μM) was found to be a poor inhibitor against all glycosidases tested, except α-galactosidases (from recombinant human α-Gal-A and coffee beans).

In addition, both compounds 17 and 33 exhibited no toxic effect in cell culture in the concentration up to 200 μM (data not shown).

Example 3 Chaperon Effects of Compounds 28 and 29

Two analogues of compound 17, including compounds 28 and 29 were prepared in accordance with procedures described in example 1.2, and their effects toward rh-α-Gal A as compared with that of compound 17 were investigated by direct measurement of the enzyme activity; and by thermal shift study.

It was found that the inhibition activities of 17, 28, and 29 against rh-α-Gal A at pH 7.0 were 0.053, 9.5, and 22.1 μM, respectively.

Figure 4:
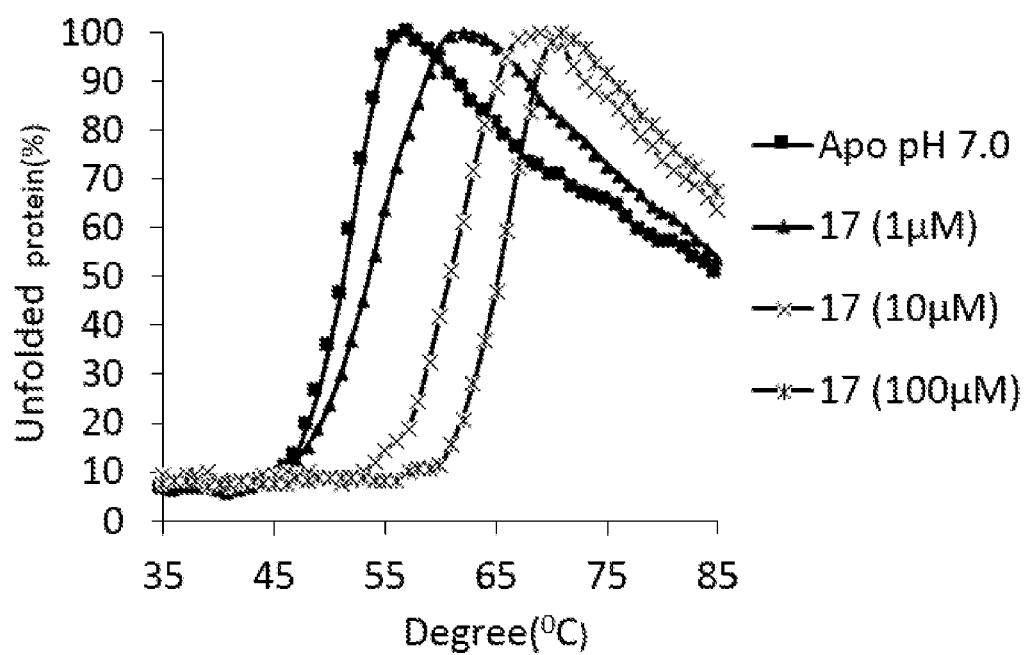
FIG. 4 illustrates the effect of compound 17 on the melting temperature of rha-Gal A in accordance with one embodiment of the present disclosure.

The thermal shift study, which is a fluorescence-based thermal denaturation assay, was employed to see if any of compounds 17, 28 or 29 improved the stabilization of rh-α-Gal A by measured the melting temperature (Tm) of the enzyme under various conditions. Results are summarized in Table 5 and FIG. 4.

The Tm of rh-α-Gal A was 51.3° C. at neutral pH (7.0), and was 54.8° C. at acidic pH (4.6), which indicated that rh-α-Gal A was relatively unstable at neutral pH. In the case when compound 17 was included in the enzyme solution at neutral pH, a concentration-dependent stabilization of rha-Gal A was found, for the Tm of rh-α-Gal A shifted from 51.3° C.→53.5° C.→60.8° C.→65.2° C. with the addition of 1, 10, and 100 μM of compound 17, respectively. By contrast, neither compound 28 nor compound 29, exhibited the same concentration-dependent stabilization effect toward rha-Gal A.

TABLE 5

Effects of compounds 17, 28, or 29 on the melting temperature of rhα-Gal A

| | Compound Tm (° C.) | | |
|---|---|---|---|
| Concentration | 28 | 29 | 17 |
| 0 μM (pH 4.6) | 54.8 | 54.8 | 54.8 |
| 0 μM (pH 7.0) | 51.3 | 51.3 | 51.3 |
| 1 μM (pH 7.0) | 51.5 | 51.3 | 53.5 |
| 10 μM (pH 7.0) | 52.3 | 51.7 | 60.8 |
| 100 μM (pH 7.0) | 56 | 53.8 | 65.2 |

Interestingly, the trend of the stabilized ability of these analogues (i.e., compounds 28 and 29) observed in thermal shift assay was similar with the trend of their inhibition activities.

Example 4 Syngergistic Effects of Co-Administrating Compound 17 and α-Gal a

In this example, the combinational use of chemical chaperone 17 and rh-α-Gal A in the enzyme replacement therapy of FD patients were investigated. Briefly, rh-α-Gal A (1 nM) and various concentrations of compound 17 (0, 1, 10, and 50 μM) were added to cultured lymophocyte of Fabry patient-derived cell line N215S, and the α-Gal A activity was then determined. Results are depicted in FIG. 5.

Figure 5:
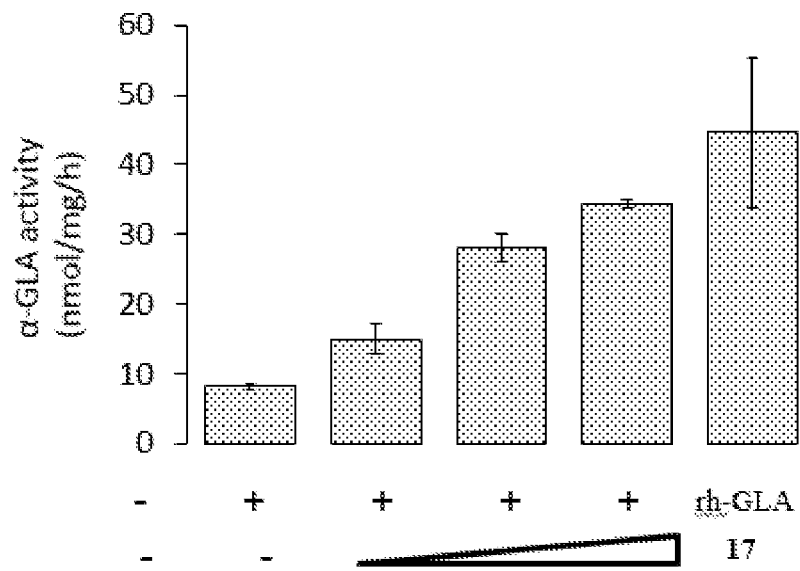
FIG. 5 illustrates the effect of (a) co-administering compound 17 and α-Gal A or (b) administering compound 17 alone to Fabry patient cell line N125S, in accordance with one embodiment of the present disclosure.
Figure 5:
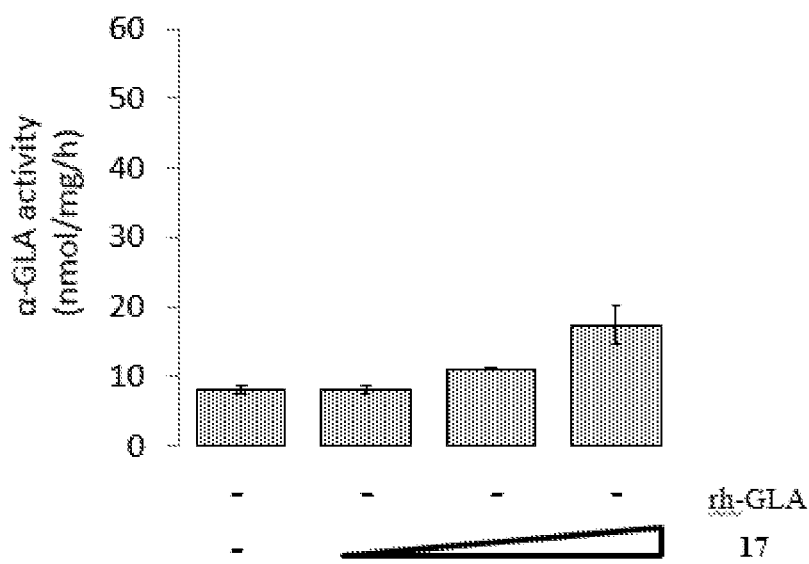

It was found that compound 17 alone was useful as a chemical chaperone to enhance intracellular lysosomal-α-Gal A activity, in which about 2-folds increase in intracellular lysosomal-α-Gal A activity was observed in the presence of 50 μM of compound 17, as compared with that of the control (FIG. 5, panel B). Most importantly, the overall α-Gal A activity increased dramatically (approximately 9-folds) when the compound 17 (50 μM) was co-administered with rh-α-Gal A (1 nM) (FIG. 5, panel A). This synergistic effect between compound 17 (chemical chaperone therapy) and rh-α-Gal A (ERT) in Fabry cell line N215S was significant, as compared to that of rh-α-Gal A or 17 alone.

Taken together, the present compound of formula (I), particularly, compound 17, is not only a α-Gal A inhibitor, but also a chemical chaperon that enhances intracellular enzyme activities in FD patients associated with mutated α-Gal A. Furthermore, compound 17 may be co-administered with α-Gal A, so as to induce synergistic effects toward intracellular α-Gal A activities.

Example 5 Chaperon Effects of Compound 33

In this example, the durability of chaperone behavior of compound 33 toward N215S lymphocytes was investigated. The test compound was added to the culture medium of N215S lymphocytes at a concentration of 0-50 μM for 4 days, and then the medium was refreshed. Cells were subsequently incubated for 0, 2, or 4 days in the absence of the test compound. After being washed twice with PBS, the enzyme activity of cell homogenates was determined with 4-MU-α-Gal as the substrate. Results are presented in FIG. 6.

Figure 6:
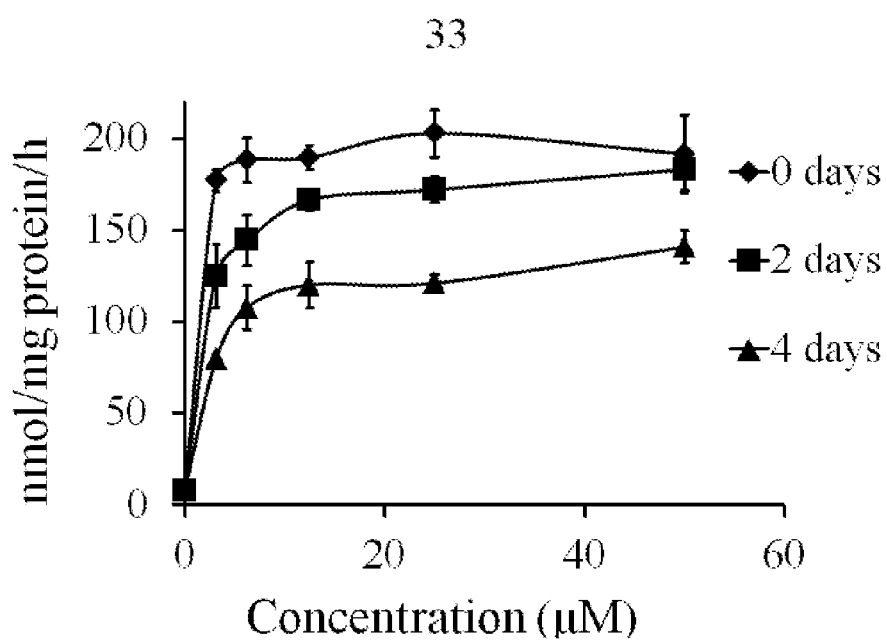
FIG. 6 illustrates the durability of chaperoning behavior of (a) compound 33 and (b) DGJ toward N125S in accordance with one embodiment of the present disclosure.
Figure 6:
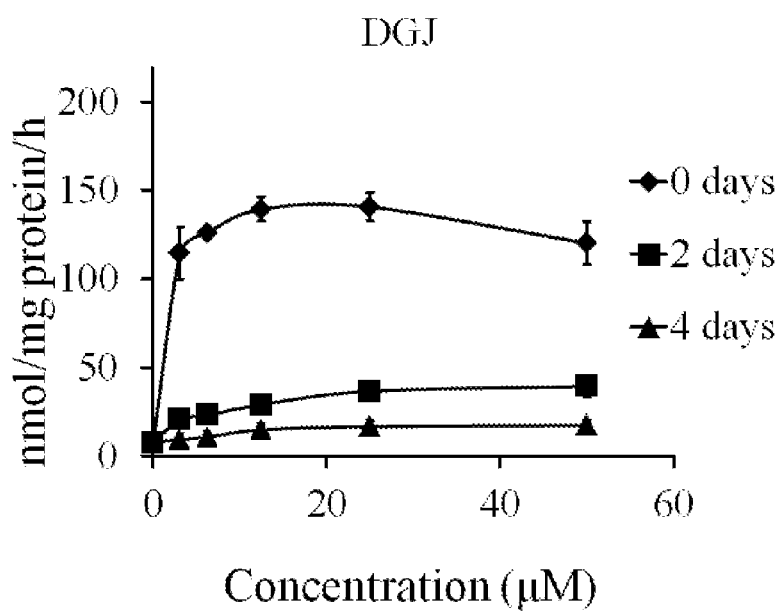

As depicted in FIG. 6, the shape of the activity curve shifted slightly with time. All pulsed concentrations resulted in significant enhancement of enzyme activity during the chase period (from 0 to 4 days), indicating that the enzyme synthesized in the presence of 33 was stable in these cells for at least four days. Following the same conditions with the pharmacological chaperone DGJ, the enzyme activity in N215S lymphocytes was still elevated after removal of DGJ, but the enhancement enzyme activity was dramatically decreased after 4 days.

Taken together, compound 33 may qualify as a new pharmacological chaperone toward N215S Fabry patient lymphocyte cells and other human α-Gal A mutants in COS7 cells. Although its inhibition activity against rh α-Gal A is not as potent as DGJ or DIA, its chaperoning activity toward N215S Fabry patient lymphocyte cells or other human α-Gal A mutants in COS7 cells is satisfactory.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of the present disclosure.

What is claimed is:

1. A method of treating a subject having or suspected of having Fabry disease comprising administering to the subject a therapeutically effective amount of a compound of formula (I), a salt, an ester or a solvate thereof,

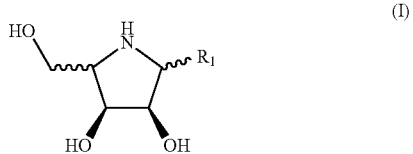

(I)

wherein:
$R_1$ is $C_{1-3}$ amine optionally substituted with —$COR_2$;
$R_2$ is alkyl or alkene optionally substituted with cycloalkyl or phenyl having at least one substituent selected from the group consisting of, halo, alkyl, haloalkyl, and alkoxyl;
so as to ameliorate, alleviate, mitigate or prevent symptoms associated with the Fabry disease.

2. The method of claim 1, wherein the compound of formula (I) is capable of suppressing α-GAL A activity.

3. The method of claim 2, wherein the compound of formula (I) is a chaperon of a human lysosomal α-galactosidase A (α-Gal A) mutant.

4. The method of claim 3, wherein the human α-Gal A mutant comprises a mutation selected from the group consisting of, R112H, P205T, Q279E, R301Q, R356W, and R363C.

5. The method of claim 4, wherein the compound of formula (I) is selected from the group consisting of,

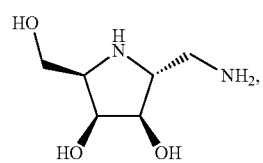

17

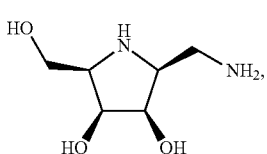

18

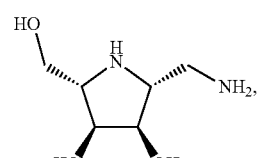

29

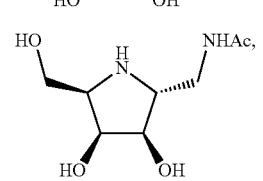

33

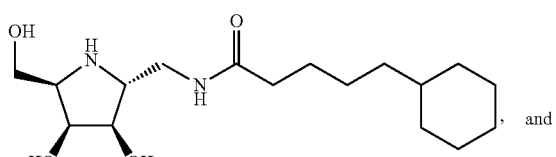

, and

37

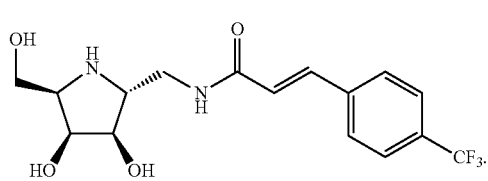

6. The method of claim 5, further comprising administering to the subject a therapeutically effective amount of human α-Gal A, prior to, concurrently with, or after the administration of the compound of formula (I).

7. The method of claim 6, wherein the compound of formula (I) is

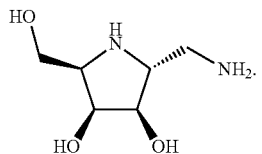

17

8. The method of claim 6, wherein the compound of formula (I) is

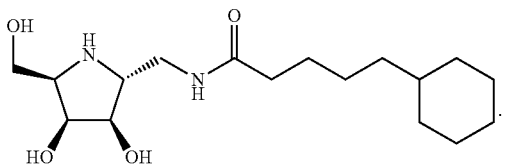

33

9. The method of claim 6, wherein the compound of formula (I) is

37

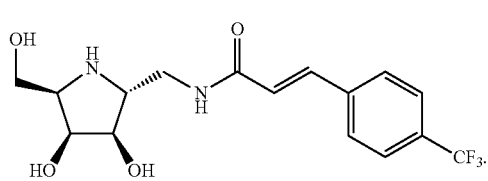

10. The method of claim 5, wherein the compound of formula (I) is administered to the subject in the amount of 0.001-500 g/day.

11. The method of claim 10, wherein the compound of formula (I) is administered to the subject in the amount of 0.05-450 g/day.

* * * * *